United States Patent
Appley et al.

(10) Patent No.: US 11,401,204 B2
(45) Date of Patent: Aug. 2, 2022

(54) UNCURED ARTICLES WITH IMPROVED SHELF-LIFE

(71) Applicants: KNAUF INSULATION SPRL, Visé (BE); KNAUF INSULATION, INC., Shelbyville, IN (US)

(72) Inventors: Charles Fitch Appley, Cumberland, IN (US); Gert Mueller, New Palestine, IN (US)

(73) Assignees: Knauf Insulation, Inc., Shelbyville, IN (US); Knauf Insulation SPRL, Vise (BE)

( * ) Notice: Subject to any disclaimer, the term of this patent is extended or adjusted under 35 U.S.C. 154(b) by 600 days.

(21) Appl. No.: 15/116,254

(22) PCT Filed: Feb. 6, 2015

(86) PCT No.: PCT/US2015/014786
§ 371 (c)(1),
(2) Date: Aug. 3, 2016

(87) PCT Pub. No.: WO2015/120252
PCT Pub. Date: Aug. 13, 2015

(65) Prior Publication Data
US 2016/0347652 A1    Dec. 1, 2016

Related U.S. Application Data

(60) Provisional application No. 61/937,110, filed on Feb. 7, 2014.

(51) Int. Cl.
| | | |
|---|---|---|
| *E04B 1/88* | (2006.01) | |
| *C03C 13/06* | (2006.01) | |
| *C03C 25/32* | (2018.01) | |
| *C07H 3/02* | (2006.01) | |
| *C03C 25/1095* | (2018.01) | |
| *F16L 59/02* | (2006.01) | |

(52) U.S. Cl.
CPC .......... *C03C 13/06* (2013.01); *C03C 25/1095* (2013.01); *C03C 25/32* (2013.01); *C07H 3/02* (2013.01); *F16L 59/028* (2013.01)

(58) Field of Classification Search
None
See application file for complete search history.

(56) References Cited

U.S. PATENT DOCUMENTS

| | | |
|---|---|---|
| 1,801,052 A | 4/1931 | Meigs |
| 1,801,053 A | 4/1931 | Meigs |
| 1,886,353 A | 11/1932 | Novotny et al. |
| 1,902,948 A | 3/1933 | Castle |
| 1,964,263 A | 6/1934 | Krenke |
| 2,198,874 A | 4/1940 | Leighton |
| 2,215,825 A | 9/1940 | Wallace et al. |
| 2,261,295 A | 11/1941 | Schlack |
| 2,362,086 A | 11/1944 | Eastes et al. |
| 2,371,990 A | 3/1945 | Hanford |
| 2,392,105 A | 1/1946 | Sussman |
| 2,442,989 A | 6/1948 | Sussman |
| 2,500,665 A | 3/1950 | Courtright |
| 2,518,956 A | 8/1950 | Sussman |
| 2,875,073 A | 2/1959 | Gogek |
| 2,894,920 A | 7/1959 | Ramos |
| 2,965,504 A | 12/1960 | Gogek |
| 3,038,462 A | 6/1962 | Bohdan |
| 3,138,473 A | 6/1964 | Floyd et al. |
| 3,222,243 A | 12/1965 | Gaston et al. |
| 3,231,349 A | 1/1966 | Stalego |
| 3,232,821 A | 2/1966 | Banks et al. |
| 3,297,419 A | 1/1967 | Eyre, Jr. |
| 3,513,001 A | 5/1970 | Woodhead et al. |
| 3,551,365 A | 12/1970 | Matalon |
| 3,784,408 A | 1/1974 | Jaffe et al. |
| 3,791,807 A | 2/1974 | Etzel et al. |
| 3,802,897 A | 4/1974 | Voigt et al. |
| 3,809,664 A | 5/1974 | Burr et al. |
| 3,826,767 A | 7/1974 | Hoover et al. |
| 3,856,606 A | 12/1974 | Fan et al. |
| 3,867,119 A | 2/1975 | Takeo et al. |
| 3,907,724 A | 9/1975 | Higginbottom |
| 3,911,048 A | 10/1975 | Vargiu et al. |
| 3,919,134 A | 11/1975 | Higginbottom |
| 3,922,466 A | 11/1975 | Bell et al. |

(Continued)

FOREIGN PATENT DOCUMENTS

| | | |
|---|---|---|
| AU | 8538765 | 8/1985 |
| AU | 9640921 | 7/1997 |

(Continued)

OTHER PUBLICATIONS

Written Opinion of International Searching Authority for PCT/US2015/014786, dated Aug. 13, 2015, 6 pages.
International Search Report and Written Opinion for PCT/US2008/059730, completed Sep. 22, 2008.
International Search Report and Written Opinion for PCT/US2008/069046, completed Sep. 25, 2008.
International Search Report and Written Opinion for PCT/EP2011/059317, completed Jul. 15, 2011.
International Search Report for PCT/EP2008/060185, completed Oct. 23, 2008.
International Search Report for PCT/EP2011/057363, completed Sep. 5, 2011.
Ames, J.M., "The Maillard Browning Reaction—an Update," Chemistry & Industry, No. 17, 1988, 4 pages.

(Continued)

*Primary Examiner* — Yun Qian
(74) *Attorney, Agent, or Firm* — Knauf Insulation, Inc.; James K. Blodgett

(57) ABSTRACT

Disclosed are formaldehyde-free, thermally-curable, alkaline, aqueous binder compositions. Also disclosed are compositions comprising formaldehyde-free, thermally-curable binder compositions, as described herein, applied to non-woven fibers. Uses of the disclosed binder compositions as binders for non-woven fibers are also disclosed.

16 Claims, No Drawings

(56) References Cited

U.S. PATENT DOCUMENTS

| | | |
|---|---|---|
| 3,955,031 A | 5/1976 | Jones et al. |
| 3,956,204 A | 5/1976 | Higginbottom |
| 3,961,081 A | 6/1976 | McKenzie |
| 3,971,807 A | 7/1976 | Brack |
| 4,014,726 A | 3/1977 | Fargo |
| 4,028,290 A | 6/1977 | Reid |
| 4,048,127 A | 9/1977 | Gibbons et al. |
| 4,054,713 A | 10/1977 | Sakaguchi et al. |
| 4,085,076 A | 4/1978 | Gibbons et al. |
| 4,097,427 A | 6/1978 | Aitken et al. |
| 4,107,379 A | 8/1978 | Stofko |
| 4,109,057 A | 8/1978 | Nakamura et al. |
| 4,144,027 A | 3/1979 | Habib |
| 4,148,765 A | 4/1979 | Nelson |
| 4,183,997 A | 1/1980 | Stofko |
| 4,184,986 A | 1/1980 | Krasnobajew et al. |
| 4,186,053 A | 1/1980 | Krasnobajew et al. |
| 4,201,247 A | 5/1980 | Shannon |
| 4,201,857 A | 5/1980 | Krasnobajew et al. |
| 4,217,414 A | 8/1980 | Walon |
| 4,233,432 A | 11/1980 | Curtis, Jr. |
| 4,246,367 A | 1/1981 | Curtis, Jr. |
| 4,259,190 A | 3/1981 | Fahey |
| 4,265,963 A | 5/1981 | Matalon |
| 4,278,573 A | 7/1981 | Tessler |
| 4,296,173 A | 10/1981 | Fahey |
| 4,301,310 A | 11/1981 | Wagner |
| 4,310,585 A | 1/1982 | Shannon |
| 4,322,523 A | 3/1982 | Wagner |
| 4,330,443 A | 5/1982 | Rankin |
| 4,333,484 A | 6/1982 | Keritsis |
| 4,357,194 A | 11/1982 | Stofko |
| 4,361,588 A | 11/1982 | Herz |
| 4,379,101 A | 4/1983 | Smith |
| 4,393,019 A | 7/1983 | Geimer |
| 4,396,430 A | 8/1983 | Matalon |
| 4,400,496 A | 8/1983 | Butler et al. |
| 4,464,523 A | 8/1984 | Neigel et al. |
| 4,506,684 A | 3/1985 | Keritsis |
| 4,520,143 A | 5/1985 | Jellinek |
| 4,524,164 A | 6/1985 | Viswanathan et al. |
| 4,631,226 A | 12/1986 | Jellinek |
| 4,654,259 A | 3/1987 | Stofko |
| 4,668,716 A | 5/1987 | Pepe et al. |
| 4,692,478 A | 9/1987 | Viswanathan et al. |
| 4,714,727 A | 12/1987 | Hume, III |
| 4,720,295 A | 1/1988 | Bronshtein |
| 4,734,996 A | 4/1988 | Kim et al. |
| 4,754,056 A | 6/1988 | Ansel et al. |
| 4,761,184 A | 8/1988 | Markessini |
| 4,780,339 A | 10/1988 | Lacourse et al. |
| 4,828,643 A | 5/1989 | Newman et al. |
| 4,845,162 A | 7/1989 | Schmitt et al. |
| 4,906,237 A | 3/1990 | Johansson et al. |
| 4,912,147 A | 3/1990 | Pfoehler et al. |
| 4,918,861 A | 4/1990 | Carpenter et al. |
| 4,923,980 A | 5/1990 | Blomberg |
| 4,950,444 A | 8/1990 | Deboufie et al. |
| 4,988,780 A | 1/1991 | Das et al. |
| 4,992,519 A | 2/1991 | Mukherjee |
| 5,001,202 A | 3/1991 | Denis et al. |
| 5,013,405 A | 5/1991 | Izard |
| 5,032,431 A | 7/1991 | Conner et al. |
| 5,037,930 A | 8/1991 | Shih |
| 5,041,595 A | 8/1991 | Yang et al. |
| 5,089,342 A | 2/1992 | Dhein et al. |
| 5,095,054 A | 3/1992 | Lay et al. |
| 5,106,615 A | 4/1992 | Dikstein |
| 5,114,004 A | 5/1992 | Isono et al. |
| 5,123,949 A | 6/1992 | Thiessen |
| 5,124,369 A | 6/1992 | Vandichel et al. |
| 5,128,407 A | 7/1992 | Layton et al. |
| 5,143,582 A | 9/1992 | Arkens et al. |
| 5,151,465 A | 9/1992 | Le-Khac |
| 5,167,738 A | 12/1992 | Bichot et al. |
| 5,198,492 A | 3/1993 | Stack |
| 5,217,741 A | 6/1993 | Kawachi et al. |
| 5,218,048 A | 6/1993 | Abe et al. |
| 5,240,498 A | 8/1993 | Matalon et al. |
| 5,244,474 A | 9/1993 | Lorcks et al. |
| 5,278,222 A | 1/1994 | Stack |
| 5,300,144 A | 4/1994 | Adams |
| 5,300,192 A | 4/1994 | Hansen et al. |
| 5,308,896 A | 5/1994 | Hansen et al. |
| 5,318,990 A | 6/1994 | Strauss |
| 5,336,753 A | 8/1994 | Jung et al. |
| 5,336,755 A | 8/1994 | Pape |
| 5,336,766 A | 8/1994 | Koga et al. |
| 5,340,868 A | 8/1994 | Strauss et al. |
| 5,352,480 A | 10/1994 | Hansen et al. |
| 5,367,849 A | 11/1994 | Bullock |
| 5,371,194 A | 12/1994 | Ferretti |
| 5,387,665 A | 2/1995 | Misawa et al. |
| 5,389,716 A | 2/1995 | Graves |
| 5,393,849 A | 2/1995 | Srinivasan et al. |
| 5,416,139 A | 5/1995 | Zeiszler |
| 5,421,838 A | 6/1995 | Gosset et al. |
| 5,424,418 A | 6/1995 | Duflot |
| 5,434,233 A | 7/1995 | Kiely et al. |
| 5,447,977 A | 9/1995 | Hansen et al. |
| 5,470,843 A | 11/1995 | Stahl et al. |
| 5,480,973 A | 1/1996 | Goodlad et al. |
| 5,492,756 A | 2/1996 | Seale et al. |
| 5,498,662 A | 3/1996 | Tanaka et al. |
| 5,503,920 A | 4/1996 | Alkire et al. |
| 5,534,612 A | 7/1996 | Taylor et al. |
| 5,536,766 A | 7/1996 | Seyffer et al. |
| 5,538,783 A | 7/1996 | Hansen et al. |
| 5,543,215 A | 8/1996 | Hansen et al. |
| 5,545,279 A | 8/1996 | Hall et al. |
| 5,547,541 A | 8/1996 | Hansen et al. |
| 5,547,745 A | 8/1996 | Hansen et al. |
| 5,550,189 A | 8/1996 | Qin et al. |
| 5,554,730 A | 9/1996 | Woiszwillo et al. |
| 5,562,740 A | 10/1996 | Cook et al. |
| 5,571,618 A | 11/1996 | Hansen et al. |
| 5,578,678 A | 11/1996 | Hartmann et al. |
| 5,580,856 A | 12/1996 | Prestrelski et al. |
| 5,582,682 A | 12/1996 | Ferretti |
| 5,583,193 A | 12/1996 | Aravindakshan et al. |
| 5,589,256 A | 12/1996 | Hansen et al. |
| 5,589,536 A | 12/1996 | Golino et al. |
| 5,607,759 A | 3/1997 | Hansen et al. |
| 5,608,011 A | 3/1997 | Eck et al. |
| 5,609,727 A | 3/1997 | Hansen et al. |
| 5,614,570 A | 3/1997 | Hansen et al. |
| 5,620,940 A | 4/1997 | Birbara et al. |
| 5,621,026 A | 4/1997 | Tanaka et al. |
| 5,633,298 A | 5/1997 | Arfaei et al. |
| 5,641,561 A | 6/1997 | Hansen et al. |
| 5,643,978 A | 7/1997 | Darwin et al. |
| 5,645,756 A | 7/1997 | Dubin et al. |
| 5,660,904 A | 8/1997 | Andersen et al. |
| 5,661,213 A | 8/1997 | Arkens et al. |
| 5,670,585 A | 9/1997 | Taylor et al. |
| 5,672,418 A | 9/1997 | Hansen et al. |
| 5,672,659 A | 9/1997 | Shalaby et al. |
| 5,690,715 A | 11/1997 | Schiwek |
| 5,691,060 A | 11/1997 | Levy |
| 5,693,411 A | 12/1997 | Hansen et al. |
| 5,719,092 A | 2/1998 | Arrington |
| 5,719,228 A | 2/1998 | Taylor et al. |
| 5,733,624 A | 3/1998 | Syme et al. |
| 5,756,580 A | 5/1998 | Natori et al. |
| 5,763,524 A | 6/1998 | Arkens et al. |
| 5,788,243 A | 8/1998 | Harshaw et al. |
| 5,788,423 A | 8/1998 | Perkins |
| 5,807,364 A | 9/1998 | Hansen |
| 5,855,987 A | 1/1999 | Margel et al. |
| 5,863,985 A | 1/1999 | Shalaby et al. |
| 5,885,337 A | 3/1999 | Nohr et al. |
| 5,895,804 A | 4/1999 | Lee et al. |
| 5,905,115 A | 5/1999 | Luitjes et al. |
| 5,916,503 A | 6/1999 | Rettenbacher |

(56) References Cited

U.S. PATENT DOCUMENTS

| | | |
|---|---|---|
| 5,919,528 A | 7/1999 | Huijs et al. |
| 5,919,831 A | 7/1999 | Philipp |
| 5,922,403 A | 7/1999 | Tecle |
| 5,925,722 A | 7/1999 | Exner et al. |
| 5,929,184 A | 7/1999 | Holmes-Farley et al. |
| 5,929,196 A | 7/1999 | Kissel et al. |
| 5,932,344 A | 8/1999 | Ikemoto et al. |
| 5,932,665 A | 8/1999 | DePorter et al. |
| 5,932,689 A | 8/1999 | Arkens et al. |
| 5,942,123 A | 8/1999 | McArdle |
| 5,954,869 A | 9/1999 | Elfersy et al. |
| 5,977,224 A | 11/1999 | Cheung et al. |
| 5,977,232 A | 11/1999 | Arkens et al. |
| 5,981,719 A | 11/1999 | Woiszwillo et al. |
| 5,983,586 A | 11/1999 | Berdan, II et al. |
| 5,990,216 A | 11/1999 | Cai et al. |
| 5,993,709 A | 11/1999 | Bonomo et al. |
| 6,022,615 A | 2/2000 | Rettenbacher |
| 6,067,821 A | 5/2000 | Jackson et al. |
| 6,071,549 A | 6/2000 | Hansen |
| 6,071,994 A | 6/2000 | Hummerich et al. |
| 6,072,086 A | 6/2000 | James et al. |
| 6,077,883 A | 6/2000 | Taylor et al. |
| 6,090,925 A | 7/2000 | Woiszwillo et al. |
| 6,114,033 A | 9/2000 | Ikemoto et al. |
| 6,114,464 A | 9/2000 | Reck et al. |
| 6,133,347 A | 10/2000 | Vickers, Jr. et al. |
| 6,136,916 A | 10/2000 | Arkens et al. |
| 6,139,619 A | 10/2000 | Zaretskiy et al. |
| 6,143,243 A | 11/2000 | Gershun et al. |
| 6,171,444 B1 | 1/2001 | Nigam |
| 6,171,654 B1 | 1/2001 | Salsman et al. |
| 6,180,037 B1 | 1/2001 | Andersen et al. |
| 6,194,512 B1 | 2/2001 | Chen et al. |
| 6,210,472 B1 | 4/2001 | Kwan et al. |
| 6,221,958 B1 | 4/2001 | Shalaby et al. |
| 6,221,973 B1 | 4/2001 | Arkens et al. |
| 6,231,721 B1 | 5/2001 | Quick et al. |
| 6,274,661 B1 | 8/2001 | Chen et al. |
| 6,281,298 B1 | 8/2001 | Papsin, Jr. |
| 6,299,677 B1 | 10/2001 | Johnson et al. |
| 6,299,936 B1 | 10/2001 | Reck et al. |
| 6,307,732 B1 | 10/2001 | Tsubaki et al. |
| 6,310,227 B1 | 10/2001 | Sarama et al. |
| 6,313,102 B1 | 11/2001 | Colaco et al. |
| 6,319,683 B1 | 11/2001 | James et al. |
| 6,331,350 B1 | 12/2001 | Taylor et al. |
| 6,331,513 B1 | 12/2001 | Zaid et al. |
| 6,340,411 B1 | 1/2002 | Hansen et al. |
| 6,348,530 B1 | 2/2002 | Reck et al. |
| 6,365,079 B1 | 4/2002 | Winkler et al. |
| 6,372,077 B1 | 4/2002 | Tecle |
| 6,379,739 B1 | 4/2002 | Formanek et al. |
| 6,379,814 B1 | 4/2002 | Dupre et al. |
| 6,395,856 B1 | 5/2002 | Petty et al. |
| 6,403,665 B1 | 6/2002 | Sieker et al. |
| 6,407,225 B1 | 6/2002 | Mang et al. |
| 6,410,036 B1 | 6/2002 | De Rosa et al. |
| 6,440,204 B1 | 8/2002 | Rogols et al. |
| 6,441,122 B1 | 8/2002 | DeMott et al. |
| 6,461,553 B1 | 10/2002 | Hansen et al. |
| 6,468,442 B2 | 10/2002 | Bytnar |
| 6,468,730 B2 | 10/2002 | Fujiwara et al. |
| 6,469,120 B1 | 10/2002 | Elfersy et al. |
| 6,475,552 B1 | 11/2002 | Shah et al. |
| 6,482,875 B2 | 11/2002 | Lorenz et al. |
| 6,495,656 B1 | 12/2002 | Haile et al. |
| 6,521,339 B1 | 2/2003 | Hansen et al. |
| 6,525,009 B2 | 2/2003 | Sachdev et al. |
| 6,538,057 B1 | 3/2003 | Wildburg et al. |
| 6,547,867 B2 | 4/2003 | Rogols et al. |
| 6,555,616 B1 | 4/2003 | Helbing et al. |
| 6,559,302 B1 | 5/2003 | Shah et al. |
| 6,562,267 B1 | 5/2003 | Hansen et al. |
| 6,596,103 B1 | 7/2003 | Hansen et al. |
| 6,613,378 B1 | 9/2003 | Erhan et al. |
| 6,638,882 B1 | 10/2003 | Helbing et al. |
| 6,638,884 B2 | 10/2003 | Quick et al. |
| 6,699,945 B1 | 3/2004 | Chen et al. |
| 6,706,853 B1 | 3/2004 | Stanssens et al. |
| 6,719,862 B2 | 4/2004 | Quick et al. |
| 6,730,730 B1 | 5/2004 | Hansen et al. |
| 6,753,361 B2 | 6/2004 | Kroner et al. |
| 6,818,694 B2 | 11/2004 | Hindi et al. |
| 6,821,547 B2 | 11/2004 | Shah et al. |
| 6,852,247 B2 | 2/2005 | Bytnar |
| 6,858,074 B2 | 2/2005 | Anderson et al. |
| 6,861,495 B2 | 3/2005 | Barsotti et al. |
| 6,864,044 B2 | 3/2005 | Ishikawa et al. |
| 6,878,800 B2 | 4/2005 | Husemoen et al. |
| 6,884,849 B2 | 4/2005 | Chen et al. |
| 6,955,844 B2 | 10/2005 | Tagge et al. |
| 6,962,714 B2 | 11/2005 | Hei et al. |
| 6,989,171 B2 | 1/2006 | Portman |
| 6,992,203 B2 | 1/2006 | Trusovs |
| 7,018,490 B2 | 3/2006 | Hansen et al. |
| 7,029,717 B1 | 4/2006 | Ojima et al. |
| 7,067,579 B2 | 6/2006 | Taylor et al. |
| 7,083,831 B1 | 8/2006 | Koch et al. |
| 7,090,745 B2 | 8/2006 | Beckman et al. |
| 7,141,626 B2 | 11/2006 | Rodrigues et al. |
| 7,144,474 B1 | 12/2006 | Hansen et al. |
| 7,195,792 B2 | 3/2007 | Boston et al. |
| 7,201,778 B2 | 4/2007 | Smith et al. |
| 7,201,825 B2 | 4/2007 | Dezutter et al. |
| 7,202,326 B2 | 4/2007 | Kuroda et al. |
| 7,241,487 B2 | 7/2007 | Taylor et al. |
| 7,458,235 B2 | 12/2008 | Beaufils et al. |
| 7,514,027 B2 | 4/2009 | Horres et al. |
| 7,655,711 B2 | 2/2010 | Swift et al. |
| 7,772,347 B2 | 8/2010 | Swift et al. |
| 7,795,354 B2 | 9/2010 | Srinivasan et al. |
| 7,803,879 B2 | 9/2010 | Srinivasan et al. |
| 7,807,771 B2 | 10/2010 | Swift et al. |
| 7,842,382 B2 | 11/2010 | Helbing |
| 7,854,980 B2 | 12/2010 | Jackson et al. |
| 7,883,693 B2 | 2/2011 | Sehl et al. |
| 7,888,445 B2 | 2/2011 | Swift et al. |
| 7,947,765 B2 | 5/2011 | Swift et al. |
| 8,114,210 B2 | 2/2012 | Hampson et al. |
| 8,182,648 B2 | 5/2012 | Swift et al. |
| 8,211,923 B2 | 7/2012 | Wagner et al. |
| 8,372,900 B2 | 2/2013 | Shooshtari et al. |
| 8,377,564 B2 | 2/2013 | Shooshtari et al. |
| 8,501,838 B2 | 8/2013 | Jackson et al. |
| 8,597,532 B2 | 12/2013 | Jaffrennou et al. |
| 8,680,224 B2 | 3/2014 | Zhang et al. |
| 8,691,934 B2 | 4/2014 | Helbing, et al. |
| 8,900,495 B2 | 12/2014 | Pacorel et al. |
| 2001/0017427 A1 | 8/2001 | Rosthauser et al. |
| 2001/0046824 A1 | 11/2001 | Nigam |
| 2002/0000100 A1 | 1/2002 | Burg et al. |
| 2002/0025435 A1 | 2/2002 | Hansen et al. |
| 2002/0026025 A1 | 2/2002 | Kuo et al. |
| 2002/0028857 A1 | 3/2002 | Holy |
| 2002/0032253 A1 | 3/2002 | Lorenz et al. |
| 2002/0042473 A1 | 4/2002 | Trollsas et al. |
| 2002/0091185 A1 | 7/2002 | Taylor et al. |
| 2002/0096278 A1 | 7/2002 | Foster et al. |
| 2002/0123598 A1 | 9/2002 | Sieker et al. |
| 2002/0130439 A1 | 9/2002 | Kroner et al. |
| 2002/0161108 A1 | 10/2002 | Schultz et al. |
| 2002/0197352 A1 | 12/2002 | Portman |
| 2003/0005857 A1 | 1/2003 | Minami et al. |
| 2003/0040239 A1 | 2/2003 | Toas et al. |
| 2003/0044513 A1 | 3/2003 | Shah et al. |
| 2003/0066523 A1 | 4/2003 | Lewis et al. |
| 2003/0071879 A1 | 4/2003 | Swenson |
| 2003/0116294 A1 | 6/2003 | Kehrer et al. |
| 2003/0134945 A1 | 7/2003 | Capps |
| 2003/0148084 A1 | 8/2003 | Trocino |
| 2003/0153690 A1 | 8/2003 | Husemoen et al. |
| 2003/0185991 A1 | 10/2003 | Wigger et al. |
| 2003/0203117 A1 | 10/2003 | Bartkowiak et al. |

(56) References Cited

U.S. PATENT DOCUMENTS

| | | |
|---|---|---|
| 2004/0002567 A1 | 1/2004 | Chen et al. |
| 2004/0019168 A1 | 1/2004 | Soerens et al. |
| 2004/0024170 A1 | 2/2004 | Husemoen et al. |
| 2004/0033269 A1 | 2/2004 | Hei et al. |
| 2004/0033747 A1 | 2/2004 | Miller et al. |
| 2004/0034154 A1 | 2/2004 | Tutin et al. |
| 2004/0038017 A1 | 2/2004 | Tutin et al. |
| 2004/0048531 A1 | 3/2004 | Belmares et al. |
| 2004/0077055 A1 | 4/2004 | Fosdick et al. |
| 2004/0079499 A1 | 4/2004 | Dezutter et al. |
| 2004/0087024 A1 | 5/2004 | Bellocq et al. |
| 2004/0087719 A1 | 5/2004 | Rautschek et al. |
| 2004/0122166 A1 | 6/2004 | O'Brien-Bernini et al. |
| 2004/0131874 A1 | 7/2004 | Tutin et al. |
| 2004/0144706 A1 | 7/2004 | Beaufils et al. |
| 2004/0152824 A1 | 8/2004 | Dobrowolski |
| 2004/0161993 A1 | 8/2004 | Tripp et al. |
| 2004/0209851 A1 | 10/2004 | Nelson et al. |
| 2004/0213930 A1 | 10/2004 | Halabisky |
| 2004/0220368 A1 | 11/2004 | Li et al. |
| 2004/0249066 A1 | 12/2004 | Heinzman et al. |
| 2004/0254285 A1 | 12/2004 | Rodrigues et al. |
| 2004/0260082 A1 | 12/2004 | Van Der Wilden et al. |
| 2005/0001198 A1 | 1/2005 | Bytnar |
| 2005/0017394 A1 | 1/2005 | Hochsmann et al. |
| 2005/0027283 A1 | 2/2005 | Richard et al. |
| 2005/0033037 A1 | 2/2005 | Trusovs |
| 2005/0048212 A1 | 3/2005 | Clamen et al. |
| 2005/0059770 A1 | 3/2005 | Srinivasan et al. |
| 2005/0171085 A1 | 8/2005 | Pinto et al. |
| 2005/0196421 A1 | 9/2005 | Hunter et al. |
| 2005/0202224 A1 | 9/2005 | Helbing |
| 2005/0208852 A1 | 9/2005 | Weber |
| 2005/0215153 A1 | 9/2005 | Cossement et al. |
| 2005/0245669 A1 | 11/2005 | Clungeon et al. |
| 2005/0275133 A1 | 12/2005 | Cabell et al. |
| 2005/0288479 A1 | 12/2005 | Kuroda et al. |
| 2006/0005580 A1 | 1/2006 | Espiard et al. |
| 2006/0009569 A1 | 1/2006 | Charbonneau et al. |
| 2006/0044302 A1 | 3/2006 | Chen |
| 2006/0099870 A1 | 5/2006 | Garcia et al. |
| 2006/0111480 A1 | 5/2006 | Hansen et al. |
| 2006/0124538 A1 | 6/2006 | Morcrette et al. |
| 2006/0135433 A1 | 6/2006 | Murray et al. |
| 2006/0141177 A1 | 6/2006 | Ligtenberg et al. |
| 2006/0179892 A1 | 8/2006 | Horres et al. |
| 2006/0188465 A1 | 8/2006 | Perrier et al. |
| 2006/0198954 A1 | 9/2006 | Frechem et al. |
| 2006/0231487 A1 | 10/2006 | Bartley et al. |
| 2006/0252855 A1 | 11/2006 | Pisanova et al. |
| 2006/0281622 A1 | 12/2006 | Maricourt et al. |
| 2007/0006390 A1 | 1/2007 | Clamen et al. |
| 2007/0009582 A1 | 1/2007 | Madsen et al. |
| 2007/0027281 A1 | 2/2007 | Michl et al. |
| 2007/0039520 A1 | 2/2007 | Crews et al. |
| 2007/0082983 A1 | 4/2007 | Crews et al. |
| 2007/0123679 A1 | 5/2007 | Swift et al. |
| 2007/0123680 A1 | 5/2007 | Swift et al. |
| 2007/0129522 A1 | 6/2007 | Burckhardt et al. |
| 2007/0142596 A1 | 6/2007 | Swift et al. |
| 2007/0158022 A1 | 7/2007 | Heep et al. |
| 2007/0184740 A1 | 8/2007 | Keller et al. |
| 2007/0191574 A1 | 8/2007 | Miller et al. |
| 2007/0270070 A1 | 11/2007 | Othman |
| 2007/0287018 A1 | 12/2007 | Tutin et al. |
| 2007/0292618 A1 | 12/2007 | Srinivasan et al. |
| 2007/0292619 A1 | 12/2007 | Srinivasan et al. |
| 2007/0298274 A1 | 12/2007 | Eriksson et al. |
| 2008/0009209 A1 | 1/2008 | Clamen et al. |
| 2008/0009616 A1 | 1/2008 | Frank et al. |
| 2008/0051539 A1 | 2/2008 | Kelly |
| 2008/0060551 A1 | 3/2008 | Crews et al. |
| 2008/0081138 A1 | 4/2008 | Moore et al. |
| 2008/0108741 A1 | 5/2008 | Van Herwijnen et al. |
| 2008/0160260 A1 | 7/2008 | Wada et al. |
| 2008/0160302 A1 | 7/2008 | Asrar et al. |
| 2008/0194738 A1 | 8/2008 | Crews et al. |
| 2009/0169867 A1 | 7/2009 | Kelly |
| 2009/0170978 A1 | 7/2009 | Kelly |
| 2009/0227732 A1 | 9/2009 | Glockner et al. |
| 2009/0301972 A1 | 12/2009 | Hines et al. |
| 2009/0304919 A1 | 12/2009 | Wagner et al. |
| 2009/0306255 A1 | 12/2009 | Patel et al. |
| 2009/0324915 A1 | 12/2009 | Swift et al. |
| 2010/0029160 A1 | 2/2010 | Srinivasan et al. |
| 2010/0058661 A1 | 3/2010 | Jackson et al. |
| 2010/0080976 A1 | 4/2010 | Jackson et al. |
| 2010/0084598 A1 | 4/2010 | Jackson et al. |
| 2010/0086726 A1 | 4/2010 | Jackson et al. |
| 2010/0087571 A1 | 4/2010 | Jackson et al. |
| 2010/0098947 A1 | 4/2010 | Inoue et al. |
| 2010/0117023 A1 | 5/2010 | Dopico et al. |
| 2010/0129640 A1 | 5/2010 | Kelly |
| 2010/0130649 A1 | 5/2010 | Swift et al. |
| 2010/0175826 A1 | 7/2010 | Huenig et al. |
| 2010/0210595 A1 | 8/2010 | Wagner et al. |
| 2010/0222463 A1 | 9/2010 | Brady et al. |
| 2010/0222566 A1 | 9/2010 | Fosdick et al. |
| 2010/0282996 A1 | 11/2010 | Jaffrennou et al. |
| 2010/0301256 A1 | 12/2010 | Hampson et al. |
| 2010/0320113 A1 | 12/2010 | Swift |
| 2011/0021672 A1 | 1/2011 | Crews et al. |
| 2011/0039111 A1 | 2/2011 | Shooshtari |
| 2011/0040010 A1 | 2/2011 | Shooshtari |
| 2011/0042303 A1 | 2/2011 | Shooshtari et al. |
| 2011/0045966 A1 | 2/2011 | Shooshtari et al. |
| 2011/0089074 A1 | 4/2011 | Jackson et al. |
| 2011/0135937 A1 | 6/2011 | Swift et al. |
| 2011/0190425 A1 | 8/2011 | Swift |
| 2011/0220835 A1 | 9/2011 | Swift et al. |
| 2011/0256790 A1 | 10/2011 | Toas et al. |
| 2011/0260094 A1 | 10/2011 | Hampson et al. |
| 2011/0262648 A1 | 10/2011 | Lee et al. |
| 2011/0263757 A1 | 10/2011 | Rand et al. |
| 2011/0306726 A1 | 12/2011 | Bailey et al. |
| 2012/0133073 A1 | 5/2012 | Pacorel et al. |
| 2012/0156954 A1 | 6/2012 | Eckert et al. |
| 2013/0029150 A1* | 1/2013 | Appley .................. C08J 5/24 428/391 |
| 2013/0032749 A1 | 2/2013 | Jaffrennou et al. |
| 2013/0047888 A1 | 2/2013 | Mueller et al. |
| 2013/0059075 A1 | 3/2013 | Appley et al. |
| 2013/0082205 A1 | 4/2013 | Mueller et al. |
| 2013/0140481 A1 | 6/2013 | Naerum et al. |
| 2013/0174758 A1 | 7/2013 | Mueller |
| 2013/0234362 A1 | 9/2013 | Swift et al. |
| 2013/0236650 A1 | 9/2013 | Swift et al. |
| 2013/0237113 A1 | 9/2013 | Swift et al. |
| 2013/0244524 A1 | 9/2013 | Swift et al. |
| 2013/0327250 A1 | 12/2013 | Shooshtari |
| 2014/0091247 A1 | 4/2014 | Jackson et al. |
| 2014/0120348 A1 | 5/2014 | Didier et al. |
| 2014/0134909 A1 | 5/2014 | Guo et al. |
| 2014/0357787 A1 | 12/2014 | Jobber et al. |

FOREIGN PATENT DOCUMENTS

| | | |
|---|---|---|
| CA | 1090026 | 11/1980 |
| CA | 2037214 | 9/1991 |
| CA | 2232334 | 11/1998 |
| CA | 2458333 | 12/1999 |
| CA | 2278946 | 1/2000 |
| CA | 2470783 | 12/2004 |
| CN | 1251738 | 5/2000 |
| DE | 1905054 | 8/1969 |
| DE | 4142261 | 6/1993 |
| DE | 4233622 | 4/1994 |
| DE | 4308089 | 9/1994 |
| DE | 102004033561 | 9/2005 |
| DE | 102005023431 | 11/2006 |
| EP | 0044614 A2 | 1/1982 |
| EP | 0099801 | 2/1984 |
| EP | 0310258 A2 | 4/1989 |
| EP | 354023 | 2/1990 |

(56) References Cited

FOREIGN PATENT DOCUMENTS

| | | |
|---|---|---|
| EP | 0375235 A1 | 6/1990 |
| EP | 0461995 | 12/1991 |
| EP | 0524518 A2 | 1/1993 |
| EP | 0547819 A2 | 6/1993 |
| EP | 0583086 A1 | 2/1994 |
| EP | 0714754 A2 | 6/1996 |
| EP | 796681 | 9/1997 |
| EP | 0826710 A2 | 3/1998 |
| EP | 856494 | 8/1998 |
| EP | 0873976 A1 | 10/1998 |
| EP | 878135 | 11/1998 |
| EP | 0882756 A2 | 12/1998 |
| EP | 0911361 A1 | 4/1999 |
| EP | 915811 | 5/1999 |
| EP | 936060 | 8/1999 |
| EP | 976866 | 2/2000 |
| EP | 0990729 A1 | 4/2000 |
| EP | 1038433 A1 | 9/2000 |
| EP | 1193288 A1 | 4/2002 |
| EP | 1084167 | 9/2002 |
| EP | 1268702 | 1/2003 |
| EP | 1382642 | 1/2004 |
| EP | 1486547 A2 | 12/2004 |
| EP | 1522642 | 4/2005 |
| EP | 1521807 B1 | 3/2006 |
| EP | 1698598 A1 | 9/2006 |
| EP | 1767566 | 4/2007 |
| EP | 2223941 A1 | 9/2010 |
| EP | 2253663 | 11/2010 |
| EP | 2457943 A1 | 10/2011 |
| EP | 2549006 B1 | 1/2013 |
| EP | 2164883 B1 | 9/2013 |
| EP | 2576882 B1 | 2/2015 |
| EP | 2969448 B1 | 8/2017 |
| FR | 2614388 | 10/1988 |
| GB | 770561 | 3/1957 |
| GB | 809675 | 3/1959 |
| GB | 926749 | 5/1963 |
| GB | 1206193 A | 9/1970 |
| GB | 1391172 | 4/1975 |
| GB | 1469331 | 4/1977 |
| GB | 1512066 | 5/1978 |
| GB | 1525541 | 9/1978 |
| GB | 2047258 | 11/1980 |
| GB | 2078805 A | 1/1982 |
| GB | 2173523 | 10/1986 |
| GB | 2251438 | 7/1992 |
| JP | 53113784 | 10/1978 |
| JP | 57101100 | 6/1982 |
| JP | 5811193 | 1/1983 |
| JP | 61195647 | 8/1986 |
| JP | 3-173680 | 7/1991 |
| JP | 05186635 | 7/1993 |
| JP | 7-034023 | 2/1995 |
| JP | 09157627 | 6/1997 |
| JP | 10234314 | 9/1998 |
| JP | 11035491 | 2/1999 |
| JP | 11181690 | 7/1999 |
| JP | 2000327841 | 11/2000 |
| JP | 2002293576 | 9/2002 |
| JP | 2003147276 | 5/2003 |
| JP | 2003238921 | 8/2003 |
| JP | 2004060058 | 2/2004 |
| JP | 2005306919 | 11/2005 |
| NZ | 549563 | 1/2008 |
| RU | 1765996 | 8/1995 |
| SU | 374400 | 3/1973 |
| WO | 1990007541 | 7/1990 |
| WO | 1992012198 | 7/1992 |
| WO | 1995034517 | 12/1995 |
| WO | 1997049646 | 12/1997 |
| WO | 1999036368 | 7/1999 |
| WO | 199947765 | 9/1999 |
| WO | 199960042 | 11/1999 |
| WO | 199960043 | 11/1999 |
| WO | 200058085 | 10/2000 |
| WO | 2001014491 | 3/2001 |
| WO | 2001059026 | 8/2001 |
| WO | 200200429 | 1/2002 |
| WO | 200206178 | 1/2002 |
| WO | 2003029496 | 4/2003 |
| WO | 2003071879 | 9/2003 |
| WO | 2003106561 | 12/2003 |
| WO | 2004007615 | 1/2004 |
| WO | 2004076734 | 9/2004 |
| WO | 2005087837 | 9/2005 |
| WO | 2006044302 | 4/2006 |
| WO | 2006136614 | 12/2006 |
| WO | 2007014236 A2 | 1/2007 |
| WO | 2007014236 A2 | 2/2007 |
| WO | 2007024020 A1 | 3/2007 |
| WO | 2007050964 | 5/2007 |
| WO | 2007112335 | 10/2007 |
| WO | 2008089847 | 7/2008 |
| WO | 2008089851 | 7/2008 |
| WO | 2008127936 A2 | 10/2008 |
| WO | 2008141201 | 11/2008 |
| WO | 2009019235 A1 | 2/2009 |
| WO | 2009129084 | 10/2009 |
| WO | 2010027937 | 3/2010 |
| WO | 2010106181 A1 | 9/2010 |
| WO | 2010139899 | 12/2010 |
| WO | 2011019590 | 2/2011 |
| WO | 2011019593 | 2/2011 |
| WO | 2011019597 | 2/2011 |
| WO | 2011019598 | 2/2011 |
| WO | 2011022224 | 2/2011 |
| WO | 2011022226 | 2/2011 |
| WO | 2011022227 | 2/2011 |
| WO | 2011123593 A1 | 10/2011 |
| WO | WO 2011123592 | * 10/2011 ................ F25B 1/00 |
| WO | 2011138458 | 11/2011 |
| WO | 2011138459 | 11/2011 |
| WO | 2011154368 A1 | 12/2011 |
| WO | 2013030390 A1 | 3/2013 |
| WO | 2013150123 A1 | 10/2013 |
| WO | 2013179323 A1 | 12/2013 |
| WO | 2014165176 A1 | 10/2014 |

OTHER PUBLICATIONS

"Gamma-aminopropyltrimethoxysilane," Hawley's Condensed Chemical Dictionary, 14th Edition, John Wiley & Sons, Inc., 2002, 1 page.

Hodge, J.E., Chemistry of Browning Reactions in Model Systems, 1953, J. Agric. Food Chem., vol. 1, No. 15, pp. 928-943.

Agyei-Aye et al., "The Role of Anion in the Reaction of Reducing Sugars with Ammonium Salts," Carbohydrate Research 2002, 337: 2273-2277.

Laroque et al., "Kinetic study on the Maillard reaction. Consideration of sugar reactivity," Food Chemistry 2008, 111: 1032-1042.

Bjorksten et al., "Polyester Resin—Glass Fiber Laminates," Industrial and Engineering Chemistry (1954).

Dow Corning, "A Guide to Silane Solutions," 2005.

Knauf Data Sheet, 2006.

Molasses Corporation, United States Sugar Corporation, http://www.suga-lik.com/molasses/composition.html (Sep. 29, 2003).

Clamen, Guy, "Acrylic Thermosets: A Safe Alternative to Formaldehyde Resins," Nonwovens World, Apr.-May 2004, pp. 96-102.

Opposition to AU 2006272595, Amended Statement of Grounds and Particulars, issued from Australian Patent Office, Jul. 6, 2012, 22 pages.

Decision re Opposition to AU 2006272595, issued from Australian Patent Office, Aug. 14, 2015, 25 pages.

Opposition to EP 1732968, Notice of Opposition: Prior Art, Scope of the Patent, Reasons for the Opposition, issued from European Patent Office, Mar. 8, 2012, 18 pages.

Decision re Opposition to EP 1732968, issued from the European Patent Office, Nov. 14, 2014, 5 pages.

Opposition to EA 019802, submitted to Eurasian Patent Office on Dec. 26, 2014, 36 pages.

(56) References Cited

OTHER PUBLICATIONS

Decision re Opposition to EA 019802, issued by Eurasian Patent Office on Aug. 18, 2015, 15 pages.
Owens Corning Retiree Update: What Goes Around, Comes Around: A tale of Natural Binders, revised Mar. 20, 2013 p. 4.
A.P. Bryant, "The Terminology of Sugars," Industrial and Engineering Chemistry, vol. 26, No. 2, p. 231, Feb. 1934.
Food Flavor Chemistry, p. 162, Mar. 21, 2009 (English Abstract).
Viswanathan, T., "Chapter 28: Thermosetting Adhesive Resins from Whey and Whey Byproducts," in Adhesives from Renewable Resources, ACS Symposium Series, Hemingway, R.W., et al. (Eds.), American Chemical Society, Washington, DC (1989).
Viswanathan, T., and Richardson, T., "Thermosetting Adhesive Resins from Whey and Whey Byproducts," Ind. Eng. Chem. Prod. Res. Dev. 23:644-47, American Chemical Society, United States (1984).
Residential Energy Conservation: vol. 1, Congress of the U.S., Office of Technology Assessment (Ed.), 357 pages (Jan. 1, 1979).
Office action for co-pending U.S. Appl. No. 12/524,502 (9 pages)—dated Sep. 21, 2012.
Office action for co-pending U.S. Appl. No. 12/524,502 (9 pages)—dated Apr. 4, 2013.
Office action for co-pending U.S. Appl. No. 12/524,512 (7 pages)—dated Aug. 6, 2012.
Office action for co-pending U.S. Appl. No. 12/524,512 (9 pages)—dated Apr. 1, 2013.
Office action for co-pending U.S. Appl. No. 12/524,512 (14 pages)—dated Nov. 12, 2014.
Office action for co-pending U.S. Appl. No. 12/524,512 (9 pages)—dated Jul. 10, 2015.
Office action for co-pending U.S. Appl. No. 12/524,512 (10 pages)—dated Mar. 23, 2016.
Office action for co-pending U.S. Appl. No. 12/524,512 (13 pages)—dated Oct. 5, 2016.
Office action for co-pending U.S. Appl. No. 12/524,512 (13 pages)—dated Apr. 6, 2018.
Office action for co-pending U.S. Appl. No. 12/524,512 (15 pages)—dated Jan. 17, 2019.
Office action for co-pending U.S. Appl. No. 12/524,469 (7 pages)—dated Jun. 7, 2012.
Office action for co-pending U.S. Appl. No. 12/524,469 (8 pages)—dated Jan. 29, 2013.
Office action for co-pending U.S. Appl. No. 12/524,469 (7 pages)—dated Aug. 20, 2013.
Office action for co-pending U.S. Appl. No. 12/524,469 (9 pages)—dated Jun. 9, 2014.
Office action for co-pending U.S. Appl. No. 12/524,469 (9 pages)—dated Oct. 17, 2014.
Office action for co-pending U.S. Appl. No. 12/524,469 (9 pages)—dated Jul. 23, 2015.
Office action for co-pending U.S. Appl. No. 12/524,539 (13 pages)—dated Jun. 21, 2012.
Office action for co-pending U.S. Appl. No. 12/524,539 (13 pages)—dated Jun. 6, 2013.
Office action for co-pending U.S. Appl. No. 12/524,539 (12 pages)—dated Dec. 17, 2014.
Office action for co-pending U.S. Appl. No. 12/524,539 (7 pages)—dated Jul. 15, 2015.
Office action for co-pending U.S. Appl. No. 12/524,539 (7 pages)—dated Mar. 23, 2016.
Office action for co-pending U.S. Appl. No. 12/524,539 (7 pages)—dated Dec. 29, 2016.
Office action for co-pending U.S. Appl. No. 12/524,522 (4 pages)—dated Oct. 11, 2011.
Office action for co-pending U.S. Appl. No. 12/667,718 (5 pages)—dated Sep. 3, 2013.
Office action for co-pending U.S. Appl. No. 12/667,718 (6 pages)—dated Sep. 9, 2014.
Office action for co-pending U.S. Appl. No. 12/671,922 (10 pages)—dated Oct. 7, 2011.
Office action for co-pending U.S. Appl. No. 12/671,922 (10 pages)—dated May 10, 2012.
Office action for co-pending U.S. Appl. No. 12/671,922 (9 pages)—dated Sep. 23, 2014.
Office action for co-pending U.S. Appl. No. 12/671,922 (5 pages)—dated Apr. 4, 2016.
Office action for co-pending U.S. Appl. No. 13/388,408 (5 pages)—dated Aug. 15, 2013.
Office action for co-pending U.S. Appl. No. 13/371,829 (9 pages)—dated Dec. 20, 2012.
Office action for co-pending U.S. Appl. No. 13/371,829 (6 pages)—dated Jul. 12, 2013.
Office action for co-pending U.S. Appl. No. 13/371,829 (6 pages)—dated Aug. 12, 2014.
Office action for co-pending U.S. Appl. No. 13/637,794 (8 pages)—dated Aug. 12, 2013.
Office action for co-pending U.S. Appl. No. 13/637,794 (9 pages)—dated Mar. 26, 2014.
Office action for co-pending U.S. Appl. No. 13/696,439 (11 pages)—dated Jan. 8, 2014.
Office action for co-pending U.S. Appl. No. 13/696,452 (7 pages)—dated Jan. 13, 2015.
Office action for co-pending U.S. Appl. No. 13/696,452 (9 pages)—dated Oct. 27, 2015.
Office action for co-pending U.S. Appl. No. 13/702,144 (6 pages)—dated Jan. 10, 2014.
Office action for co-pending U.S. Appl. No. 13/702,144 (7 pages)—dated Jul. 29, 2014.
Office action for co-pending U.S. Appl. No. 13/823,818 (9 pages)—dated Mar. 26, 2015.
Office action for co-pending U.S. Appl. No. 13/866,368 (16 pages)—dated Aug. 29, 2013.
Office action for co-pending U.S. Appl. No. 13/866,368 (11 pages)—dated Apr. 16, 2014.
Office action for co-pending U.S. Appl. No. 13/866,368 (8 pages)—dated Aug. 21, 2014.
Office action for co-pending U.S. Appl. No. 13/866,419 (14 pages)—dated Sep. 20, 2013.
Office action for co-pending U.S. Appl. No. 13/866,419 (10 pages)—dated Apr. 25, 2014.
Office action for co-pending U.S. Appl. No. 13/866,419 (8 pages)—dated Oct. 9, 2014.
Office action for co-pending U.S. Appl. No. 13/866,419 (8 pages)—dated Sep. 25, 2015.
Office action for co-pending U.S. Appl. No. 13/868,233 (23 pages)—dated Aug. 13, 2013.
Office action for co-pending U.S. Appl. No. 13/868,233 (12 pages)—dated Apr. 15, 2014.
Office action for co-pending U.S. Appl. No. 13/868,233 (8 pages)—dated Oct. 7, 2014.
Office action for co-pending U.S. Appl. No. 13/868,233 (8 pages)—dated Jul. 16, 2015.
Office action for co-pending U.S. Appl. No. 13/868,238 (8 pages)—dated Jul. 16, 2014.
Office action for co-pending U.S. Appl. No. 12/976,379 (7 pages)—dated Jan. 10, 2012.
Office action for co-pending U.S. Appl. No. 12/976,379 (6 pages)—dated Jul. 27, 2012.
Office action for co-pending U.S. Appl. No. 12/976,379 (9 pages)—dated Mar. 7, 2013.
Office action for co-pending U.S. Appl. No. 12/976,379 (8 pages)—dated Aug. 20, 2013.
Office action for co-pending U.S. Appl. No. 12/599,858 (8 pages)—dated May 11, 2011.
Office action for co-pending U.S. Appl. No. 13/341,542 (8 pages)—dated Dec. 26, 2012.
Office action for co-pending U.S. Appl. No. 13/341,542 (7 pages)—dated Feb. 10, 2014.
Office action for co-pending U.S. Appl. No. 14/026,394 (6 pages)—dated Aug. 14, 2014.
Office action for co-pending U.S. Appl. No. 14/272,556 (14 pages)—dated Nov. 20, 2014.

(56) References Cited

OTHER PUBLICATIONS

Office action for co-pending U.S. Appl. No. 14/272,556 (12 pages)—dated Sep. 17, 2015.
Office action for co-pending U.S. Appl. No. 14/342,069 (17 pages)—dated Dec. 29, 2015.
Office action for co-pending U.S. Appl. No. 14/342,069 (22 pages)—dated Sep. 2, 2016.
Office action for co-pending U.S. Appl. No. 14/342,069 (21 pages)—dated Sep. 26, 2017.
Office action for co-pending U.S. Appl. No. 14/342,069 (21 pages)—dated Jun. 6, 2018.
Office action for co-pending U.S. Appl. No. 14/649,277 (9 pages)—dated Jul. 22, 2016.
Office action for co-pending U.S. Appl. No. 14/686,915 (8 pages)—dated Nov. 18, 2016.
Office action for co-pending U.S. Appl. No. 14/810,765 (7 pages)—dated Jan. 29, 2016.
Office action for co-pending U.S. Appl. No. 14/828,916 (8 pages)—dated Nov. 25, 2016.
Office action for co-pending U.S. Appl. No. 14/867,502 (9 pages)—dated Nov. 18, 2016.
Office action for co-pending U.S. Appl. No. 15/172,432 (16 pages)—dated Apr. 17, 2017.
Office action for co-pending U.S. Appl. No. 15/702,087 (5 pages)—dated Nov. 9, 2018.
Office action for co-pending U.S. Appl. No. 15/177,442 (17 pages)—dated May 19, 2017.
Office action for co-pending U.S. Appl. No. 15/378,159 (18 pages)—dated Mar. 2, 2017.
Office action for co-pending U.S. Appl. No. 15/222,122 (8 pages)—dated Nov. 20, 2017.
Office action for co-pending U.S. Appl. No. 15/310,837 (13 pages)—dated Jun. 21, 2018.
Office action for co-pending U.S. Appl. No. 15/411,972 (9 pages)—dated Mar. 28, 2017.
Office action for co-pending U.S. Appl. No. 15/411,972 (8 pages)—dated Nov. 29, 2017.
Office action for co-pending U.S. Appl. No. 15/411,972 (9 pages)—dated Jun. 14, 2018.
Office action for co-pending U.S. Appl. No. 15/116,254 (8 pages)—dated Apr. 26, 2018.
Office action for co-pending U.S. Appl. No. 15/116,254 (10 pages)—dated Aug. 15, 2018.
Office action for co-pending U.S. Appl. No. 15/333,670 (5 pages)—dated Dec. 8, 2017.
Office Action for co-pending U.S. Appl. No. 14/116,048 (10 pages)—dated Jun. 23, 2017.
Office action for co-pending U.S. Appl. No. 15/959,131 (8 pages)—dated Nov. 8, 2019.
Office action for co-pending U.S. Appl. No. 15/822,102 (6 pages)—dated Dec. 6, 2019.
Office action for co-pending U.S. Appl. No. 15/690,623 (6 pages)—dated Jan. 9, 2020.
Other Information—Narrative of verbal disclosure of Brian Swift (1 page)—dated May 13, 2014.
Petition for Inter Partes Review of U.S. Pat. No. 8,114,210 (52 pages, filed Jun. 12, 2015 by Petitioners Johns Manville Corporation and Johns Manville, Inc.).
Declaration of Dr. Frederick J. Hirsekorn Regarding U.S. Pat. No. 8,114,210 (58 pages, filed Jun. 12, 2015 by Petitioners Johns Manville Corporation and Johns Manville, Inc. in connection with Petition for Inter Partes Review of U.S. Pat. No. 8,114,210).
1st Petition for Inter Partes Review of U.S. Pat. No. D. 631,670 (68 pages, filed Jun. 19, 2015 by Petitioners Johns Manville Corporation and Johns Manville, Inc.).
2nd Petition for Inter Partes Review of U.S. Pat. No. D. 631,670 (62 pages, filed Nov. 2, 2015 by Petitioners Johns Manville Corporation and Johns Manville, Inc.).
Decision of PTAB regarding Institution of Inter Partes Review for U.S. Pat. No. D. 631,670 (33 pages)—Jan. 12, 2016.
Decision2 of PTAB regarding Institution of Inter Partes Review for U.S. Pat. No. D. 631,670 (27 pages)—May 9, 2016.
Final Written Decision of PTAB regarding Inter Partes Review of D. 631,670 based on 1st Petition (56 pages)—Jan. 11, 2017.
Final Written Decision of PTAB regarding Inter Partes Review of D. 631,670 based on 2nd Petition (55 pages)—May 8, 2017.
Court of Appeals for Federal Circuit Judgment from Appeal of PTAB Decisions in Inter Partes Reviews of U.S. Pat. No. D. 631,670 (2 pages)—Jul. 13, 2018.
1st Petition for Inter Partes Review of U.S. Pat. No. 8,940,089 (61 pages, filed Jul. 1, 2015 by Petitioners Johns Manville Corporation and Johns Manville, Inc.).
Declaration of Dr. Frederick J. Hirsekorn Regarding U.S. Pat. No. 8,940,089 (70 pages, filed Jul. 1, 2015 by Petitioners Johns Manville Corporation and Johns Manville, Inc. in connection with 1st Petition for Inter Partes Review of U.S. Pat. No. 8,940,089).
2nd Petition for Inter Partes Review of U.S. Pat. No. 8,940,089 (56 pages, filed Jul. 10, 2015 by Petitioners Johns Manville Corporation and Johns Manville, Inc.).
Declaration of Dr. Frederick J. Hirsekorn Regarding U.S. Pat. No. 8,940,089 (67 pages, filed Jul. 10, 2015 by Petitioners Johns Manville Corporation and Johns Manville, Inc. in connection with 2nd Petition for Inter Partes Review of U.S. Pat. No. 8,940,089).
3rd Petition for Inter Partes Review of U.S. Pat. No. 8,940,089 (62 pages, filed Jul. 17, 2015 by Petitioners Johns Manville Corporation and Johns Manville, Inc.).
Declaration of Dr. Frederick J. Hirsekorn Regarding U.S. Pat. No. 8,940,089 (76 pages, filed Jul. 17, 2015 by Petitioners Johns Manville Corporation and Johns Manville, Inc. in connection with 3rd Petition for Inter Partes Review of U.S. Pat. No. 8,940,089).
Declaration of Dr. Elam Leed (11 pages, filed Jul. 1, Jul. 10, and Jul. 17, 2015 by Petitioners Johns Manville Corporation and Johns Manville, Inc. in connection with 1st, 2nd and 3rd Petition for Inter Partes Review of U.S. Pat. No. 8,940,089, respectively).
Declaration of Dr. Jonathan Vickers (10 pages, filed Jul. 1, Jul. 10, and Jul. 17, 2015 by Petitioners Johns Manville Corporation and Johns Manville, Inc. in connection with 1st, 2nd and 3rd Petition for Inter Partes Review of U.S. Pat. No. 8,940,089, respectively).
1st Petition for Inter Partes Review of U.S. Pat. No. 9,039,827 (60 pages, filed Jul. 29, 2015 by Petitioners Johns Manville Corporation and Johns Manville, Inc.).
Declaration of Dr. Frederick J. Hirsekorn Regarding U.S. Pat. No. 9,039,827 (72 pages, filed Jul. 29, 2015 by Petitioners Johns Manville Corporation and Johns Manville, Inc. in connection with $1^{st}$ Petition for Inter Partes Review of U.S. Pat. No. 9,039,827).
2nd Petition for Inter Partes Review of U.S. Pat. No. 9,039,827 (51 pages, filed Aug. 5, 2015 by Petitioners Johns Manville Corporation and Johns Manville, Inc.).
Declaration of Dr. Frederick J. Hirsekorn Regarding U.S. Pat. No. 9,039,827 (65 pages, filed Aug. 5, 2015 by Petitioners Johns Manville Corporation and Johns Manville, Inc. in connection with $2^{nd}$ Petition for Inter Partes Review of U.S. Pat. No. 9,039,827).
3rd Petition for Inter Partes Review of U.S. Pat. No. 9,039,827 (57 pages, filed Aug. 7, 2015 by Petitioners Johns Manville Corporation and Johns Manville, Inc.).
Declaration of Dr. Frederick J. Hirsekorn Regarding U.S. Pat. No. 9,039,827 (75 pages, filed Aug. 7, 2015 by Petitioners Johns Manville Corporation and Johns Manville, Inc. in connection with $3^{rd}$ Petition for Inter Partes Review of U.S. Pat. No. 9,039,827).
Declaration of Dr. Elam Leed (11 pages, filed Jul. 29, Aug. 5, and Aug. 7, 2015 by Petitioners Johns Manville Corporation and Johns Manville, Inc. in connection with 1st, 2nd and 3rd Petition for Inter Partes Review of U.S. Pat. No. 9,039,827, respectively).
Declaration of Dr. Jonathan Vickers (10 pages, filed Jul. 29, Aug. 5, and Aug. 7, 2015 by Petitioners Johns Manville Corporation and Johns Manville, Inc. in connection with 1st, 2nd and 3rd Petition for Inter Partes Review of U.S. Pat. No. 9,039,827, respectively).
Petition for Inter Partes Review of U.S. Pat. No. 9,469,747 (67 pages, filed Mar. 20, 2018 by Petitioners Johns Manville Corporation and Johns Manville, Inc.).
Petition for Inter Partes Review of U.S. Pat. No. 9,828,287 (86 pages, filed Mar. 23, 2018 by Petitioners Johns Manville Corporation and Johns Manville, Inc.).

(56) References Cited

OTHER PUBLICATIONS

Petition for Inter Partes Review of U.S. Pat. No. 9,464,207 (78 pages, filed Mar. 28, 2018 by Petitioners Johns Manville Corporation and Johns Manville, Inc.).
Petition for Inter Partes Review of U.S. Pat. No. 9,926,464 (74 pages, filed Mar. 30, 2018 by Petitioners Johns Manville Corporation and Johns Manville, Inc.).
Office Action Granting Ex Parte Reexamination of U.S. Pat. No. 7,888,445, dated Dec. 24, 2013, in Control No. 90/013,029, 11 pages.
Office Action Granting Ex Parte Reexamination of U.S. Pat. No. 7,772,347, dated Dec. 24, 2013, in Control No. 90/013,030, 14 pages.
Office Action Granting Ex Parte Reexamination of U.S. Pat. No. 7,854,980, dated Apr. 15, 2014, in Control No. 90/013,156, 20 pages.
Declaration of Jan Rud Andersen submitted in Ex parte Reexamination Control No. 90/013,030, as Document OTH-C, Oct. 10, 2013, 4 pages.
Final Rejection in Ex Parte Reexamination of U.S. Pat. No. 7,888,445 (20 pages)—dated Jul. 24, 2015.
Final Rejection in Ex Parte Reexamination of U.S. Pat. No. 7,772,347 (23 pages)—dated Jul. 24, 2015.
Final Rejection in Ex Parte Reexamination of U.S. Pat. No. 7,854,980 (31 pages)—dated Aug. 18, 2015.
Advisory Action in Ex Parte Reexamination of U.S. Pat. No. 7,888,445 (4 pages)—dated Oct. 6, 2015.
Advisory Action in Ex Parte Reexamination of U.S. Pat. No. 7,772,347 (4 pages)—dated Oct. 6, 2015.
Advisory Action in Ex Parte Reexamination of U.S. Pat. No. 7,854,980 (4 pages)—dated Nov. 18, 2015.
Examiner's Answer in Ex Parte Reexamination of U.S. Pat. No. 7,888,445 (8 pages)—Mar. 23, 2016.
Examiner's Answer in Ex Parte Reexamination of U.S. Pat. No. 7,772,347 (8 pages)—Mar. 23, 2016.
Examiner's Answer in Ex Parte Reexamination of U.S. Pat. No. 7,854,980 (8 pages)—Mar. 22, 2016.
Decision of PTAB in Ex Parte Reexamination of U.S. Pat. No. 7,888,445 (17 pages)—Sep. 29, 2016.
Decision of PTAB in Ex Parte Reexamination of U.S. Pat. No. 7,772,347 (18 pages)—Sep. 29, 2016.
Decision of PTAB in Ex Parte Reexamination of U.S. Pat. No. 7,854,980 (22 pages)—Sep. 30, 2016.
Court of Appeals for Federal Circuit Judgment from Consolidated Appeal of PTAB Decisions in Ex Parte Reexamination of U.S. Pat. No. 7,888,445, 7,772,347 and 7,854,980 (5 pages)—Mar. 9, 2018.
Notice of Intent to Issue Ex Parte Reexamination Certificate for U.S. Pat. No. 7,772,347 (4 pages)—dated Oct. 24, 2018.
Notice of Intent to Issue Ex Parte Reexamination Certificate for U.S. Pat. No. 7,888,445 (4 pages)—dated Dec. 7, 2018.
Notice of Intent to Issue Inter Partes Reexamination Certificate for U.S. Pat. No. 7,888,445 (14 pages)—dated Sep. 24, 2020.
Notice of Intent to Issue Inter Partes Reexamination Certificate for U.S. Pat. No. 7,772,347 (13 pages)—dated Sep. 25, 2020.
Decision of USPTO to Reopen Prosecution in Ex Parte Reexamination of U.S. Pat. No. 7,854,980 (7 pages)—Jan. 7, 2019.
Non-final Office Action from Reopened Prosecution in Ex Parte Reexamination of U.S. Pat. No. 7,854,980 (26 pages)—dated Apr. 3, 2019.
Final Office Action from Reopened Prosecution in Ex Parte Reexamination of U.S. Pat. No. 7,854,980 (11 pages)—dated Aug. 8, 2019.
Notice of Intent to Issue Ex Parte Reexamination Certificate for U.S. Pat. No. 7,854,980 (3 pages)—dated Oct. 29, 2019.
Notice of Intent to Issue Inter Partes Reexamination Certificate for U.S. Pat. No. 7,807,771 (4 pages)—dated Jan. 30, 2014.
Notice of Intent to Issue Inter Partes Reexamination Certificate for U.S. Pat. No. 7,854,980 (6 pages)—dated Aug. 31, 2017.
Decision of PTAB in Inter Partes Reexamination of U.S. Pat. No. 7,888,445 (34 pages)—May 1, 2015.
Decision of PTAB in Inter Partes Reexamination of U.S. Pat. No. 7,772,347 (36 pages)—May 1, 2015.
Decision of PTAB in Inter Partes Reexamination of U.S. Pat. No. 7,854,980 (25 pages)—Jul. 30, 2015.
Remand Order of PTAB in Inter Partes Reexamination of U.S. Pat. No. 7,888,445 (5 pages)—Dec. 9, 2015.
Remand Order of PTAB in Inter Partes Reexamination of U.S. Pat. No. 7,772,347 (5 pages)—Dec. 9, 2015.
Examiner's Determination on Patent Owner Response/Requester Comments after Board Decision in Inter Partes Reexamination of U.S. Pat. No. 7,888,445 (22 pages)—Oct. 17, 2016.
Examiner's Determination on Patent Owner Response/Requester Comments after Board Decision in Inter Partes Reexamination of U.S. Pat. No. 7,772,347 (17 pages)—Oct. 17, 2016.
Court of Appeals for Federal Circuit Opinion/Judgment from Appeal of PTAB Decision in Inter Partes Reexamination of U.S. Pat. No. 7,854,980 (13 pages)—Feb. 27, 2017.
Final Decision of PTAB in Inter Partes Reexamination of U.S. Pat. No. 7,888,445 (25 pages)—Sep. 8, 2017.
Final Decision of PTAB in Inter Partes Reexamination of U.S. Pat. No. 7,772,347 (24 pages)—Sep. 8, 2017.
Decision of PTAB re Request for Rehearing in Inter Partes Reexamination of U.S. Pat. No. 7,888,445 (7 pages)—Feb. 12, 2018.
Decision of PTAB re Request for Rehearing in Inter Partes Reexamination of U.S. Pat. No. 7,772,347 (7 pages)—Feb. 12, 2018.
Court of Appeals for Federal Circuit Decision re Consolidated Appeal of PTAB Decision in Inter Partes Reexamination of U.S. Pat. No. 7,772,347 and U.S. Pat. No. 7,888,445 (14 pages)—Oct. 15, 2019.
Remand Order of PTAB in Inter Partes Reexamination of U.S. Pat. No. 7,888,445 (3 pages)—Jul. 1, 2020.
Remand Order of PTAB in Inter Partes Reexamination of U.S. Pat. No. 7,772,347 (3 pages)—Jul. 1, 2020.
Decision of PTAB regarding Institution of Inter Partes Review for U.S. Pat. No. 8,114,210 (20 pages)—Oct. 21, 2015.
Final Written Decision of PTAB regarding Inter Partes Review of U.S. Pat. No. 8,114,210 (39 pages)—Oct. 19, 2016.
Court of Appeals for Federal Circuit Judgment from Appeal of PTAB Decision in Inter Partes Review of U.S. Pat. No. 8,114,210 (5 pages)—Jan. 16, 2018.
Decision of USPTO Granting Ex Parte Re-exam of U.S. Pat. No. 8,114,210 (11 pages)—Apr. 9, 2020.
Decision1 of PTAB declining Institution of Inter Partes Review for U.S. Pat. No. 8,940,089 (16 pages)—Dec. 17, 2015.
Decision2 of PTAB declining Institution of Inter Partes Review for U.S. Pat. No. 8,940,089 (19 pages)—Dec. 17, 2015.
Decision3 of PTAB declining Institution of Inter Partes Review for U.S. Pat. No. 8,940,089 (14 pages)—Dec. 17, 2015.
Decision1 of PTAB declining Institution of Inter Partes Review for U.S. Pat. No. 9,039,827 (16 pages)—Jan. 4, 2016.
Decision2 of PTAB declining Institution of Inter Partes Review for U.S. Pat. No. 9,039,827 (19 pages)—Jan. 4, 2016.
Decisions3 of PTAB declining Institution of Inter Partes Review for U.S. Pat. No. 9,039,827 (14 pages)—Jan. 4, 2016.
Decision of PTAB denying Institution of Inter Partes Review for U.S. Pat. No. 9,926,464 (29 pages)—Oct. 2, 2018.
Decision of PTAB denying Institution of Inter Partes Review for U.S. Pat. No. 9,464,207 (28 pages)—Oct. 2, 2018.
Decision of PTAB denying Institution of Inter Partes Review for U.S. Pat. No. 9,469,747 (29 pages)—Oct. 3, 2018.
Decision of PTAB denying Institution of Inter Partes Review for U.S. Pat. No. 9,828,287 (22 pages)—Oct. 16, 2018.
Decision of USPTO Granting Ex Parte Re-exam of U.S. Pat. No. 9,828,287 (13 pages)—Jul. 17, 2020.
Decision of USPTO Granting Ex Parte Re-exam of U.S. Pat. No. 9,464,207 (14 pages)—Jul. 31, 2020.
Decision of USPTO Granting Ex Parte Re-exam of U.S. Pat. No. 9,926,464 (18 pages)—Aug. 5, 2020.
Decision of USPTO Granting Ex Parte Re-exam of U.S. Pat. No. 8,940,089 (17 pages)—Oct. 16, 2020.
Decision of USPTO Granting Ex Parte Re-exam of U.S. Pat. No. 9,039,827 (16 pages)—Oct. 16, 2020.

(56) References Cited

OTHER PUBLICATIONS

Decision of USPTO Granting Ex Parte Re-exam of U.S. Pat. No. 9,469,747 (16 pages)—Nov. 9, 2020.
Decision of USPTO Granting Ex Parte Re-exam of U.S. Pat. No. 9,464,207 (19 pages)—Aug. 27, 2021.
Decision of USPTO Granting Ex Parte Re-exam of U.S. Pat. No. 9,926,464 (16 pages)—Sep. 7, 2021.
Decision of USPTO Granting Ex Parte Re-exam of U.S. Pat. No. 9,469,747 (10 pages)—Sep. 16, 2021.
Decision of USPTO Granting Ex Parte Re-exam of U.S. Pat. No. 8,114,210 (13 pages)—Dec. 1, 2021.
Decision of USPTO Granting Ex Parte Re-exam of U.S. Pat. No. 8,940,089 (13 pages)—Jan. 28, 2022.
Decision of USPTO Granting Ex Parte Re-exam of U.S. Pat. No. 9,828,287 (11 pages)—Feb. 1, 2022.
Decision of USPTO Granting Ex Parte Re-exam of U.S. Pat. No. 9,039,827 (13 pages)—Feb. 1, 2022.
Notice of Intent to Issue Ex Parte Reexamination Certificate for U.S. Pat. No. 8,114,210 (4 pages)—dated May 27, 2021.
Notice of Intent to Issue Ex Parte Reexamination Certificate for U.S. Pat. No. 9,464,207 (4 pages)—dated Apr. 19, 2021.
Notice of Intent to Issue Ex Parte Reexamination Certificate for U.S. Pat. No. 9,828,287 (5 pages)—dated May 5, 2021.
Notice of Intent to Issue Ex Parte Reexamination Certificate for U.S. Pat. No. 9,926,464 (5 pages)—dated May 5, 2021.
Notice of Intent to Issue Ex Parte Reexamination Certificate for U.S. Pat. No. 9,469,747 (8 pages)—dated May 21, 2021.
Notice of Intent to Issue Ex Parte Reexamination Certificate for U.S. Pat. No. 9,039,827 (3 pages)—dated Jul. 2, 2021.
Notice of Intent to Issue Ex Parte Reexamination Certificate for U.S. Pat. No. 8,940,089 (4 pages)—dated Jul. 13, 2021.
Petition for Post Grant Review of U.S. Pat. No. 10,968,629 (50 pages, filed Jan. 6, 2022 by Petitioner Rockwool International A/S).
Statement of Revocation Grounds re GB2496951-Claimant Rockwool International (May 21, 2018, 22 pages).
Statement of Revocation Grounds re GB2451719-Claimant Rockwool International (May 18, 2018, 22 pages).
Expert Report re Revocation of GB2451719 and GB2496951-Claimant Rockwool International (Nov. 12, 2018, 11 pages).
United Kingdom Intellectual Property Office, Decision in *Rockwool International* v. *Knauf Insulation Limited*, Application under Section 72 for revocation of patents GB2451719 and GB2496951 (May 28, 2019—18 pages).
Decision of EPO Board of Appeal re Added Matter vis-á-vis EP06788492.4 (Jul. 17, 2019—14 pages).
Re U.S. Pat. No. 2,965,504—Part 1 (10 pages).
Re U.S. Pat. No. 2,965,504—Part 2 (14 pages).
Re U.S. Pat. No. 2,965,504—Part 3 (14 pages).
Gogek Attorney Comments re U.S. Pat. No. 2,965,504—Apr. 6, 1960 (3 pages).
Gogek Affidavit Under Rule 132 re U.S. Pat. No. 2,965,504—Feb. 26, 1960 (3 pages).

\* cited by examiner

UNCURED ARTICLES WITH IMPROVED SHELF-LIFE

CROSS-REFERENCE TO RELATED APPLICATION

This application is a U.S. national counterpart application of International Application Serial No. PCT/US2015/014786, filed Feb. 6, 2015, under 35 U.S.C. § 371, which claims priority under 35 U.S.C.§ 119(e) to U.S. Provisional Application Serial No. 61/937,110, filed Feb. 7, 2014, the disclosures of which are hereby incorporated herein by reference.

TECHNICAL FIELD

This invention relates to binders and binder technology applicable in the preparation of compositions that include non-woven fibers. More particularly, the present invention relates to uncured mineral wool, i.e., uncured glass wool (fiberglass) and/or uncured stone wool, products (articles) prepared with formaldehyde-free binders that are cured (e.g., by molding) in a secondary step after the corresponding uncured products are collected.

BACKGROUND

So called "shipout uncured" and "plant uncured" fiberglass insulation is manufactured with an uncured, thermosetting binder. The resulting uncured insulation products are collected, packaged into rolls, bagged, and sealed in plastic bags. At various times thereafter, the bagged insulation material is i) transported to, ii) stored at, and iii) ultimately processed via a distinct separate manufacturing sequence by, a customer to yield a finished part. This manufacturing sequence includes heat curing of the binder. The time between collection of the uncured product and curing the binder can span several days to several weeks. In the case of "shipout uncured" fiberglass insulation, the uncured product is transported to customers that require the product to have a long shelf-life during ambient storage and transportation conditions. Ideally, "shipout uncured" fiberglass insulation has a minimum shelf-life of 2 to 4 weeks.

Standard binder for "shipout uncured" and "plant uncured" fiberglass insulation has historically been based on phenol-formaldehyde (PF) binder chemistry. PF binders exhibit the disadvantage of formaldehyde emissions. Binders based on reducing sugar carbohydrates for cured product lines are known in the art. Due to an increasingly uncertain regulatory situation as it pertains to the use of formaldehyde-containing binders and/or formaldehyde-liberating products, there has been steadily increasing interest in, if not demand for, a sustainable, formaldehyde-free binder based on carbohydrates for "shipout uncured" and "plant uncured" fiberglass insulation. Heretofore, the prior art has not described such a binder, or an equivalent binder composition, for such uncured fiberglass insulation products.

Initial trials aimed at discovering a carbohydrate-based binder for uncured fiberglass insulation product lines involved dextrose as the carbohydrate source. The resulting uncured product rolls displayed major disadvantages, which included the fact that: a) the dextrose-based binder crystallized out and caused poor loft and poor recovery when unrolling the fiberglass rolls, b) the dextrose-based binder migrated to the glass surface and segregated out into binder "islands," which islands were noticeable after curing/molding as a darkly-colored dotted pattern, c) due to binder migration, the inner part of the fiberglass layer was depleted of binder whereas the outer pelt surface was binder rich, which depletion caused weakened integrity of the cured/molded product whereas binder enrichment and crystallization on the pelt surface resulted in poor handling characteristics when molding (i.e., binder rich areas tended to stick to the mold platens, which often resulted in the destruction of the molded part when removing it from the platen), and d) when a permeable membrane (e.g., non-woven glass veil) was used, binder rich spots often bled through the veil upon molding.

OBJECTS OF THE INVENTION

One object of the present invention is to provide a carbohydrate-based binder that enables the manufacture of uncured fiberglass insulation products with good shelf-life during ambient transportation and storage conditions (e.g., in winter and summer; in northern and southern climate).

Another object of the present invention is to provide a carbohydrate-based binder that does not significantly and/or noticeably migrate within finished uncured fiberglass insulation products with concomitant localized depletion of binder.

Another object of the present invention is to provide a carbohydrate-based binder that does not crystallize out in finished uncured fiberglass insulation products and thereby form dotted patterns therein after cure.

Yet another object of the present invention is to provide a carbohydrate-based binder that does not significantly and/or noticeably migrate within finished uncured fiberglass insulation products with concomitant localized enrichment of binder.

SUMMARY

One aspect of the present invention provides a carbohydrate-based binder in accordance with claim 1; the dependent claims define alternative and/or preferred embodiments.

In another illustrative aspect, the present invention provides a carbohydrate-based binder solution comprising a mixture of carbohydrates, an acid precursor derivable from an inorganic salt and/or an ammonium salt of one or more polycarboxylic acids, a source of nitrogen, and optionally ammonia.

In another illustrative aspect, the present invention provides a binder based on a mixture of carbohydrates that has a tendency to generate supersaturated aqueous solutions of sugars that do not crystallize out while storing at ambient conditions over a time span of at least 3 days, preferably over a time span of longer than 2 weeks even when in contact with fiberglass.

In another illustrative aspect, the present invention provides for a carbohydrate-based binder wherein the mixture of sugars in the binder has a lower crystallization point than dextrose.

In another illustrative aspect, the present invention provides for a carbohydrate-based binder wherein the mixture of sugars is fructose and dextrose present in high fructose corn syrup (HFCS), which is used as a carbohydrate source.

In another illustrative aspect, the present invention provides for a carbohydrate-based binder which permits close control of the ratio of moisture to binder concentration in a fiberglass product.

In another illustrative aspect, the present invention provides for a carbohydrate-based binder where impurities may be added to mixtures of fructose and dextrose (e.g., mixtures obtained by dissolving fructose and dextrose or by inverting sucrose under known conditions to invert sugar). Such impurities may be dextrins and/or maltodextrins. Another form of impurities can be generated by heating tcarbohydrate solutions to form some degradation products.

In another illustrative aspect, the present invention provides for a carbohydrate-based binder where various additives may be added to improve binder performance and processability. Typical additives known in the art include, but are not necessarily limited to, adhesion promoters, coupling agents, silanes, amino-silanes, silicones, non-aqueous moisturizers, flame retardants, additives to prevent self-heating upon curing, dedusting oils, polymeric additives (e.g., styrene-maleic anhydride copolymers, acrylic copolymers), and cross-linkers (e.g., mono-, di-, and polyfunctional amines, epoxides, isocyanates, blocked isocyanates, hydroxyl-containing compounds, and carboxy-containing compounds, as well as aldehyds and ketones.)

In another illustrative aspect, a method for treating fibers, including non-woven fibers, is enabled that includes contacting mineral fibers (e.g., glass fibers) with a thermally-curable, aqueous binder composition comprising a mixture of carbohydrates, an acid precursor derivable from an inorganic salt and/or an ammonium salt of one or more polycarboxylic acids, a source of nitrogen, and optionally ammonia, as described herein, and effecting removal of most of the water from the thermally-curable, aqueous binder composition in contact with mineral fibers.

In another illustrative aspect, a fiberglass product is described that includes a binder composition, as described herein, in contact with glass fibers, which product may be processed to form one of several types of uncured fiberglass insulation, wherein the glass fibers are present in the range from about 80% to about 99% by weight.

Binder solutions used in accordance with the present invention may be "substantially formaldehyde free", that is to say that they liberate less than 5 ppm formaldehyde as a result of drying and/or curing (or appropriate tests simulating drying and/or curing). Such binder solutions are preferably "formaldehyde free", that is the say they liberate less than 1 ppm formaldehyde in such conditions.

Products in accordance with the present invention (for example, uncured fiberglass insulation materials) may be "substantially formaldehyde free;" that is to say that they comprise less than 5 ppm or less than detectable limits of free formaldehyde and/or consist of materials which together comprise less than these amounts of free formaldehyde and/or release levels of formaldehyde in standardized tests adapted to simulate their ordinary use which allows them to be classified as having no or undetectable levels of formaldehyde release. Preferably, such products release less than 10 $\mu g/m^3$, more preferably less than 5 $\mu g/m^3$, of formaldehyde during the period of 24-48 hours from the start of testing in accordance with ISO 16000.

Additional features of the present invention will become apparent to those skilled in the art upon consideration of the following detailed description of illustrative embodiments exemplifying the best mode of carrying out the invention as presently perceived.

DETAILED DESCRIPTION

It has been found that binders according to the present invention may have at least equivalent and, in some instances, improved properties compared to, for example, the tri-ammonium citrate-dextrose system of WO 2007/ 014236 and compared to, for example, the triammonium phosphate-dextrose system of WO 2009/019235. WO 2007/ 014236 teaches binder systems based, inter alia, on a combination of a carbohydrate (for example, a reducing sugar), ammonia and a polycarboxylic acid and suggests that a Maillard type reaction may form the basis of the curing chemistry. WO 2009/019235 teaches binder systems based, inter alia, on a combination of a carbohydrate (for example, a reducing sugar), an acid precursor derivable from an inorganic salt, and ammonia and suggests that a Maillard type reaction may form the basis of the curing chemistry. It would have been thought that inclusion of a mixture of at least two carbohydrates would not have a significant effect on the properties of the resulting uncured binder, particularly if the carbohydrates are both reducing sugars. It is thus surprising that a mixture of at least two carbohydrates (e.g., dextrose and fructose) should provide improved properties in an otherwise apparently similar binder system.

Use of an acid precursor derivable from an inorganic salt may have significant advantages in terms of cost, availability and ease of handling. The acid precursor derivable from an inorganic salt of the binder solution may comprise a species selected from the group consisting of sulfates, phosphates, nitrates and carbonates. A particular advantage can be achieved by use of one or more inorganic ammonium salts, for example, an ammonium sulfate, an ammonium phosphate or an ammonium carbonate salt. An ammonium salt may provide the or part of the acid precursor and/or the or part of the source of nitrogen and/or the or part of a pH control system. An ammonium nitrate salt may also work; however, ammonium nitrate may oxidise aldehyde groups of the carbohydrate (for example, aldehyde groups in dextrose) and/or require precautions to avoid explosions.

Ammonium sulfate is particularly advantageous but ammonium phosphate may be used in addition to or instead of ammonium sulfate Ammonium phosphate may be mono-ammonium phosphate, diammonium phosphate or triammonium phosphate; it may be an ammonium hydrogen phosphate. An ammonium carbonate, alone or in combination with the other materials disclosed herein, may also provide good results. The ammonium carbonate may be an ammonium bicarbonate.

The acid precursor, particularly when this consists essentially of inorganic ammonium salt(s), may make up at least 5%, preferably at least 7%, more preferably at least 9% by dry weight of the uncured binder solution; and/or less than 25% or 20%, preferably less than 18%, more preferably less than 16% by dry weight of the uncured binder solution.

The term "consist or consisting essentially of" is intended to limit the scope of a claim to the specified materials or steps and those that do not materially affect the basic and novel characteristic(s) of the claimed invention.

The acid may comprise: a sulfuric acid, a phosphoric acid, a nitric acid or a weak acid.

The binder may comprise between 5% and 25%, preferably 10% to 20%, more preferably 15% to 20% by dry weight of acid precursor (particularly where this is an inorganic ammonium salt) to total carbohydrate (particularly when this is a mixture of reducing sugars).

A carbohydrate-based binder comprising a mixture of carbohydrates, as described herein, may alternatively or in addition contain an ammonium salt of one or more polycarboxylic acid components, where the salt is monobasic or dibasic when the polycarboxylic acid component is a dicarboxylic acid, or where the salt is monobasic, dibasic, or tribasic when the polycarboxylic acid component is a tricarboxylic acid, and so on and so forth.

As used herein, the term "ammonium" includes, but is not limited to, $^+NH_4$, $^+NH_3R^1$ and $^+NH_2R^1R^2$, where $R^1$ and $R^2$ are each independently selected in $^+NH_2R^1R^2$, and where $R^1$ and $R^2$ are selected from alkyl, cycloalkyl, alkenyl, cycloalkenyl, heterocyclyl, aryl, and heteroaryl.

The term "alkyl" refers to a saturated monovalent chain of carbon atoms, which may be optionally branched; the term "cycloalkyl" refers to a monovalent chain of carbon atoms, a portion of which forms a ring; the term "alkenyl" refers to an unsaturated monovalent chain of carbon atoms including at least one double bond, which may be optionally branched; the term "cycloalkenyl" refers to an unsaturated monovalent chain of carbon atoms, a portion of which forms a ring; the term "heterocyclyl" refers to a monovalent chain of carbon and heteroatoms, wherein the heteroatoms are selected from nitrogen, oxygen, and sulfur, a portion of which, including at least one heteroatom, form a ring; the term "aryl" refers to an aromatic mono or polycyclic ring of carbon atoms, such as phenyl, naphthyl, and the like; and the term "heteroaryl" refers to an aromatic mono or polycyclic ring of carbon atoms and at least one heteroatom selected from nitrogen, oxygen, and sulfur, such as pyridinyl, pyrimidinyl, indolyl, benzoxazolyl, and the like. It is to be understood that each of alkyl, cycloalkyl, alkenyl, cycloalkenyl, and heterocyclyl may be optionally substituted with independently selected groups such as alkyl, haloalkyl, hydroxyalkyl, aminoalkyl, carboxylic acid and derivatives thereof, including esters, amides, and nitriles, hydroxy, alkoxy, acyloxy, amino, alkyl and dialkylamino, acylamino, thio, and the like, and combinations thereof It is further to be understood that each of aryl and heteroaryl may be optionally substituted with one or more independently selected substituents, such as halo, hydroxy, amino, alkyl or dialkylamino, alkoxy, alkylsulfonyl, cyano, nitro, and the like.

As used herein, the term "polycarboxylic acid" indicates a dicarboxylic, tricarboxylic, tetracarboxylic, pentacarboxylic, and like monomeric polycarboxylic acids, and anhydrides, and combinations thereof, as well as polymeric polycarboxylic acids, anhydrides, copolymers, and combinations thereof In one aspect, the polycarboxylic acid ammonium salt reactant is sufficiently non-volatile to maximize its ability to remain available for reaction with a mixture of carbohydrates in a Maillard reaction. In another aspect, the polycarboxylic acid ammonium salt reactant may be substituted with other chemical functional groups.

Illustratively, a monomeric polycarboxylic acid may be a dicarboxylic acid, including, but not limited to, unsaturated aliphatic dicarboxylic acids, saturated aliphatic dicarboxylic acids, aromatic dicarboxylic acids, unsaturated cyclic dicarboxylic acids, saturated cyclic dicarboxylic acids, hydroxy-substituted derivatives thereof, and the like. Or, illustratively, the polycarboxylic acid(s) itself may be a tricarboxylic acid, including, but not limited to, unsaturated aliphatic tricarboxylic acids, saturated aliphatic tricarboxylic acids, aromatic tricarboxylic acids, unsaturated cyclic tricarboxylic acids, saturated cyclic tricarboxylic acids, hydroxy-substituted derivatives thereof, and the like. It is appreciated that any such polycarboxylic acids may be optionally substituted, such as with hydroxy, halo, alkyl, alkoxy, and the like. In one variation, the polycarboxylic acid is the saturated aliphatic tricarboxylic acid, citric acid. Other suitable polycarboxylic acids are contemplated to include, but are not limited to, aconitic acid, adipic acid, azelaic acid, butane tetracarboxylic acid dihydride, butane tricarboxylic acid, chlorendic acid, citraconic acid, dicyclopentadiene-maleic acid adducts, diethylenetriamine pentaacetic acid, adducts of dipentene and maleic acid, ethylenediamine tetraacetic acid (EDTA), fully maleated rosin, maleated tall-oil fatty acids, fumaric acid, glutaric acid, isophthalic acid, itaconic acid, maleated rosin oxidized with potassium peroxide to alcohol then carboxylic acid, maleic acid, malic acid, mesaconic acid, biphenol A or bisphenol F reacted via the KOLBE-Schmidt reaction with carbon dioxide to introduce 3-4 carboxyl groups, oxalic acid, phthalic acid, sebacic acid, succinic acid, tartaric acid, terephthalic acid, tetrabromophthalic acid, tetrachlorophthalic acid, tetrahydrophthalic acid, trimellitic acid, trimesic acid, and the like, and anhydrides, and combinations thereof Illustratively, a polymeric polycarboxylic acid may be an acid, for example, polyacrylic acid, polymethacrylic acid, polymaleic acid, and like polymeric polycarboxylic acids, copolymers thereof, anhydrides thereof, and mixtures thereof Examples of commercially available polyacrylic acids include AQUASET-529 (Rohm & Haas, Philadelphia, Pa., USA), CRITERION 2000 (Kemira, Helsinki, Finland, Europe), NF1 (H. B. Fuller, St. Paul, Minn., USA), and SOKALAN (BASF, Ludwigshafen, Germany, Europe). With respect to SOKALAN, this is a water-soluble polyacrylic copolymer of acrylic acid and maleic acid, having a molecular weight of approximately 4000. AQUASET-529 is a composition containing polyacrylic acid cross-linked with glycerol, also containing sodium hypophosphite as a catalyst. CRITERION 2000 is an acidic solution of a partial salt of polyacrylic acid, having a molecular weight of approximately 2000. With respect to NF1, this is a copolymer containing carboxylic acid functionality and hydroxy functionality, as well as units with neither functionality; NF1 also contains chain transfer agents, such as sodium hypophosphite or organophosphate catalysts.

With respect to the mixture of carbohydrates in the binder described herein, it may include a mixture of two or more reducing sugars. In one aspect, any carbohydrate in said mixture should be sufficiently nonvolatile to maximize its ability to remain available for reaction with the acid precursor derivable from an inorganic salt and/or the polycarboxylic acid ammonium salt. The carbohydrate mixture may include a monosaccharide in its aldose or ketose form, including a triose, a tetrose, a pentose, a hexose, or a heptose; or a polysaccharide; or combinations thereof A carbohydrate may be a reducing sugar, or one that yields one or more reducing sugars in situ under thermal curing conditions. For example, when a triose serves as the carbohydrate in combination with other reducing sugars and/or a polysaccharide, an aldotriose sugar or a ketotriose sugar may be utilized, such as glyceraldehyde and dihydroxyacetone, respectively. When a tetrose serves as the carbohydrate in combination with other reducing sugars and/or a polysaccharide, aldotetrose sugars, such as erythrose and threose; and ketotetrose sugars, such as erythrulose, may be utilized. When a pentose serves as the carbohydrate in combination with other reducing sugars and/or a polysaccharide, aldopentose sugars, such as ribose, arabinose, xylose, and lyxose; and ketopentose sugars, such as ribulose, arabulose, xylulose, and lyxulose, may be utilized. When a hexose serves as the carbohydrate in combination with other reducing sugars and/or a polysaccharide, aldohexose sugars, such as glucose (i.e., dextrose), mannose, galactose, allose, altrose, talose, gulose, and idose; and ketohexose sugars, such as fructose, psicose, sorbose and tagatose, may be utilized. When a heptose serves as the carbohydrate reactant in combination with other reducing sugars and/or a polysaccharide, a ketoheptose sugar such as sedoheptulose may be utilized.

One or more aldotriose sugars may be used in combination with one or more ketotriose sugars. One or more aldotetrose sugars may be used in combination with one or more ketotetrose sugars. One or more aldopentose sugars may be used in combination with one or more ketopentose sugars. One or more aldohexose sugars may be used in combination with one or more ketohexose sugars.

One or more aldotriose sugars may be used in combination with one or more ketotetrose sugars. One or more aldopentose sugars may be used in combination with one or more ketohexose sugars. One or more aldohexose sugars may be used in combination with one or more ketopentose sugars. One or more ketohexose sugars may be used in combination with one or more aldotetrose sugars. And so on and so forth.

Other stereoisomers of such carbohydrates not known to occur naturally are also contemplated to be useful in preparing the binder compositions as described herein. When a polysaccharide serves as a carbohydrate in combination with monosaccharides, sucrose, lactose, maltose, starch, and cellulose may be utilized.

Furthermore, the mixture of carbohydrates in the binder described herein may be used in combination with one or more non-carbohydrate polyhydroxy reactant. Examples of non-carbohydrate polyhydroxy reactants which can be used in combination with a mixture of carbohydrates include, but are not limited to, trimethylolpropane, glycerol, pentaerythritol, polyvinyl alcohol, partially hydrolyzed polyvinyl acetate, fully hydrolyzed polyvinyl acetate, and mixtures thereof In one aspect, the non-carbohydrate polyhydroxy reactant is sufficiently nonvolatile to maximize its ability to remain available for reaction with the acid precursor derivable from an inorganic acid and/or with a monomeric or polymeric polycarboxylic acid ammonium salt. It is appreciated that the hydrophobicity of the non-carbohydrate polyhydroxy reactant may be a factor in determining the physical properties of a binder prepared as described herein.

Commercial quality high fructose corn syrup, HFCS 42, which contains 42% fructose, may be used as the mixture of carbohydrates for the binders described herein. In one illustrative embodiment, the binder described herein may be derived essentially from HFCS and an inorganic ammonium salt in aqueous solution. In another illustrative embodiment, the binder described herein may alternatively or also comprise an ammonium salt of a polycarboxylic acid, particularly a dicarboxylic acid or tricarboxylic acid, preferably citric acid.

Binders which comprise or consist essentially of the components described herein may include additives, for example, additives selected from: silanes, mineral oils, coupling agents, silicones or siloxanes (particularly for water repellency), silicon containing compounds, surfactants, hydrophilic additives, hydrophobic additives, waxes, substances useful for controlling the pH (e.g. ammonium hydroxide) and ammonia. Ammonium hydroxide when used, and indeed other additives, may provide the and/or an additional source of nitrogen. Preferably, the total quantity of additives (excluding ammonia) is less than 5% by weight (excluding the weight of water present), more preferably less than 3% or less than 2% by weight. Particularly for mineral fiber products, it is preferred to include a silane as an additive. The binder and/or binder solution may comprise at least 0.1% and/or less than 1% of a silane by dry weight. The silane may be amino substituted; it may be a silyl ether and it is believed that its presence may significantly improve the long term strength of the binder, particularly after weathering.

Preferences for the pH of the binder are: preferred, pH≥7; more preferred, pH≥8; and most preferred, pH≥9, at least in the state in which the binder is applied to a material to be bound and/or recovered in a waste water recuperation system. Such a neutral or alkaline pH of the binder may alleviate problems of corrosion of manufacturing equipment which have been encountered with some essentially acidic prior art binder systems. Such prior art binders include binders consisting essentially of polyacrylic acids or polymeric polycarboxylic acids. One particular advantage of the present invention is thus the use of a binder system that can operate in such neutral or alkaline conditions. When cured, the binder may become acidic during the curing process. However, equipment corrosion considerations are less significant in this case due to the minimal contact between the manufacturing equipment and the binder when in this state. The pH of the binder may be less than or equal to 13, preferably less than or equal to 12, 11 or 10. A preferred pH may be in the range of 7.5 to 9.5, particularly 8 to 9. Binder which has been applied to the material to be bound and is subsequently dissolved in water may have a pH of greater than 6.

It is preferred to arrange the pH of the binder solution at an appropriate level to prevent precipitation of its constituents and particularly to ensure that the acid precursor derivable from an inorganic salt remains in solution. This is particularly the case where ammonium phosphate provides the acid precursor. Better dry and/or weathered strengths and/or more homogeneous products may be achieved by using homogeneous binder solutions comprising ammonium salt acid precursors which are free from precipitates, particularly when ammonium phosphate is used and the binder solution is free from phosphate precipitates.

The binder composition may be provided in the form of an aqueous solution; it may contain free ammonia or excess ammonia in solution. A neutral or alkaline pH of the binder may be generated by an excess of alkaline groups compared with acid groups present in the binder solution, for example, due partially or substantially to the presence of ammonia in the solution. Additional ammonia may be added to the binder solution, for example 0.2%-1% by weight, or indeed more; this may help to keep a wash water system alkaline over the long term, particularly for the manufacture of mineral wool insulation.

In the case or mineral wool fibers particularly for thermal insulation products, when binder solution is sprayed onto hot mineral wool fibers just after they have been formed, the residual heat of the mineral wool fibers may cause a significant portion of any water in the binder solution to evaporate. Consequently, the mineral wool fibers which are then collected to form a bat may have binder present on them in the form of a sticky, viscous or tacky liquid. This may facilitate bonding between individual fibers via the binder.

One of the many advantages of this binder system is that it is applied, for example, by being sprayed onto mineral wool fibers, in a substantially unreacted state. The ability to apply the binder solution in a substantially unreacted state may alleviate problems associated with pre-reacting the binder components in solution which have been encountered with some prior art binder systems in which the components are pre-reacted. Such prior art binders include binders consisting essentially of pre-reacted polymers or resins which are applied to the materials to be bound. With substantially unreacted binder present in the form of a sticky, viscous or tacky liquid on the material to be bound, the reaction between the binder components may occur in a substantially dry state. One may describe the reaction as a bulk polymerization because it is occurring without the benefit of a solvent. A particular advantage of the present invention is thus the use of a binder system that can polymerize in a substantially dry state or through a bulk polymerization.

Mineral fibers used in the context of the invention may be formed by internal or external spinning. They may have a temperature in the range 20° C. to 200° C., generally 30° C. to 100° C. or 150° C., when sprayed with the binder solution. The quantity of binder solution sprayed may be used with or without additional water sprays to assist in cooling the mineral fibers to a desired temperature between their formation and their collection to form a batt.

A particular advantage of using ammonia in solution to control the pH of the binder solution applied to the mineral fibers is that at least part of the ammonia of binder solution that sticks to the fibers may flash off due to the residual heat of the mineral wool fibers. Consequently, the binder solution that coats the fibers may have a lower pH than the binder solution sprayed.

The present invention extends to a method of manufacturing a mineral fiber thermal insulation product comprising the sequential steps of: forming mineral fibers from a molten mineral mixture; spraying a substantially formaldehyde free binder solution on to the mineral fibers, the binder solution comprising: a mixture of carbohydrates (particularly a mixture of reducing sugars), an acid precursor derivable from an inorganic salt and/or an ammonium salt of a polycarboxylic acid, and a source of nitrogen; and collecting the mineral fibers to which the binder solution has been applied to form a uncured batt of mineral fibers. Wash water may be sprayed on to mineral fibers between their formation and their collection to form a bat, at least a part of the wash water having been sprayed on mineral fibers and subsequently returned to a wash water system to be reused as wash water. The binder solution may comprise wash water.

The binder may eventually be cured, for example in a curing oven; it may form a thermoset binder. In its cured form, the binder may: comprise melanoidins; and/or be thermoset; and/or be water insoluble or substantially water insoluble. The binder solution may be substantially colorless or white to off-white; upon curing, the binder may take on a dark color, particularly a dark brown color. The cured product may be dark in color, particularly dark brown in color. The binder may be free of proteins; it may be free of cellulosic feedstock. One of the many advantages of this binder system is that the extent of curing can be determined by the color. Substantially dehydrated binder appears white or off-white. Progressively cured to a greater extent, the binder appears progressively darker in color (a darker shade of brown). When applied to mineral fibers, the extent to which the mineral wool insulation has cured can be determined by its color.

When applied to the material to be bound and/or prior to curing, the binder may be free or substantially free of melanoidins and/or other reaction products derived from curing. Curing of the binder may produce glucosylamine, particularly as an intermediate product. Consequently, a cured or particularly a partially cured product may comprise glucosylamine The reaction of the binder upon curing may be essentially a Maillard type reaction as described for example in WO2007/14236. The binder may comprise polymerization products of a mixture that comprises a mixture of reducing sugars and a material selected from the group consisting of ammonium sulfate, ammonium phosphate, ammonium nitrate and ammonium carbonate.

The binder solution may be formulated by combining: a mixture of reducing sugar carbohydrates (e.g., provided by HFCS), an acid precursor derivable from an inorganic salt (preferably an ammonium sulfate or ammonium phosphate) and/or an ammonium salt of a polycarboxylic acid, a source of nitrogen, and water. The formulation may comprise optional or additional ammonia provided in the form of an aqueous ammonia solution. The water may comprise wash water or recycled process water.

Forming the binder solution from a mixture of carbohydrates, an acid precursor comprising an inorganic ammonium salt and/or an ammonium salt of a polycarboxylic acid provides one particular advantageous preparation method. This may be achieved in a simple mixing chamber which may be open and/or at atmospheric pressure. The mixture of carbohydrates and the acid precursor and/or the ammonium salt may be added in powder or liquid form. The preparation is preferably carried out at room temperature. Preferably it is not necessary to supply heat to prepare the binder solution; nevertheless, the binder solution may be heated during its preparation, for example to a temperature with the range 20° C. to 80° C., particularly where this facilitates dissolving and/or mixing of its ingredients.

The binder solution, particularly in the state applied to the material to be bound, may comprise: at least 5% 10%, 15% or 18% solids and/or less than 70% or 60% (particularly in the case of wood board applications) or less than 50%, 40% or 20% solids (particularly in the case of mineral fiber insulation applications) particularly determined as bake out solids by weight after drying at 140° C. for 2 hours.

The collection of loose matter bound together by means of the binders described herein may comprise materials selected from: fibers, fibrous materials, mineral fibers, glass fibers, stone wool fibers, cellulosic fibers (including wood fibers, wood shavings, wood particles and sawdust), wood veneers, facings, wood facings, particles, woven or non-woven materials, loosely assembled materials, woven or non-woven materials.

The loose matter may be shaped and/or dimensioned and/or molded with the aid of the binder. The material produced may be selected from: a thermal insulation material, a mineral fiber product, a wood board product (including chip board, orientated strand board, particle board, medium density fiber board, wood facing products), foundry sands.

The matter to be bound may be at a temperature in the range 20° C. to 100° C. when the binder is applied. The binder solution, particularly when applied to the loose matter, may have a viscosity appropriate for application by spraying or pouring. Its viscosity at 20° C. may be less than about 1.5 Pas, preferably less than about $1 \times 10^{-2}$ Pas, and/or greater than about $2 \times 10^{-4}$ Pas, preferably greater than about $5 \times 10^{-4}$ Pas.

EXAMPLES

The following examples illustrate specific embodiments in further detail. These examples are provided for illustrative purposes only and should not be construed as limiting the invention or the inventive concept to any particular physical configuration in any way.

An uncured binder composition was prepared as HFCS 42:Ammonium Sulfate=76.4:16 based on dry solids. HFCS 42 is commercial quality High Fructose Corn Syrup with 42% Fructose concentration. The preferred moisture content of an uncured fiberglass insulation product is 0.5% to 4%.

Example 1: For a fiberglass insulation product with 7% LOI after cure, the free moisture content of the uncured fiberglass insulation product is in the range of 0.5% to 7%

Example 2: For a fiberglass insulation product with 15% LOI after cure, the free moisture content of the uncured fiberglass insulation product is in the range of 1% to 7%.

In order to demonstrate the supersaturated nature of a carbohydrate-based binder of the present invention, a preferred uncured fiberglass insulation product from Example 2 has 5% free moisture.

The uncured fiberglass insulation product of Example 2 with an LOI of 15% contains approximately 21.5% binder solids of HFCS 42:Ammonium Sulfate=76.4:16. This corresponds to 17.8% HFCS and 3.7% Ammonium Sulfate based on dry weight of uncured product. Said uncured product has a free moisture concentration of 2.5%. The ratio of Ammonium Sulfate to free moisture is 3.7:2.5. The ratio of HFCS 42:free moisture is 17.8:2.5 At ambient temperatures (e.g., 20° C.) these ratios are beyond the solubility ratios of HFCS:Water of approximately 17.8:7.7 and HFCS:Ammonium Sulfate=3.7:5.

Molding of 9-month-old uncured fiberglass insulation made with HFCS/AS (Cured binder LOI: 15-17%; Moisture of Uncured: 1.5%-3%; product stored in PE bag at 15° C.-24° C.) was associated with essentially no crystallization, and the uncured insulation product was soft, showed good recovery, and processed well. This is in contrast to Dextrose/AS migrating and crystallizing out within 2 weeks, which illustrates an economic advantage of using HFCS.

What is claimed is:

1. A composition comprising an uncured binder disposed on mineral fibers, wherein the uncured binder consists of an aqueous mixture of (a) at least two reducing sugars comprising 1) at least one aldohexose sugar selected from the group consisting of dextrose, mannose, galactose, allose, altrose, talose, gulose, and idose; and 2) at least one ketohexose sugar selected from the group consisting of fructose, psicose, sorbose and tagatose, wherein the mixture has a lower crystallization point than a carbohydrate mixture consisting of dextrose; and (b) an acid precursor derivable from an inorganic salt selected from the group consisting of ammonium sulfate salts, ammonium phosphate salts, ammonium nitrate salts, ammonium carbonate salts and combinations thereof and/or (c) an ammonium salt of a polycarboxylic acid; optionally (d) a silicon-containing compound; and optionally (e) a corrosion inhibitor.

2. The composition of claim 1, wherein the inorganic salt is selected from the group consisting of ammonium sulfate salts, ammonium phosphate salts, ammonium carbonate salts, and combinations thereof.

3. The composition of claim 1, wherein the polycarboxylic acid is selected from the group consisting of unsaturated aliphatic polycarboxylic acids, saturated aliphatic polycarboxylic acids, aromatic polycarboxylic acids, unsaturated cyclic polycarboxylic acids, saturated cyclic polycarboxylic acids, and combinations thereof.

4. The composition of claim 1, wherein the silicon-containing compound is selected from the group consisting of gamma-aminopropyltriethoxysilane, gamma-glycidoxypropyltrimethoxysilane, and mixtures thereof.

5. The composition of claim 1, wherein the corrosion inhibitor is capable of decreasing the corrosivity of the composition.

6. The composition of claim 5, wherein the corrosion inhibitor is selected from the group consisting of dedusting oil, monoammonium phosphate, sodium metasilicate pentahydrate, and melamine.

7. The composition of claim 1, wherein the composition is a fiberglass insulation product.

8. The composition of claim 1, wherein the mineral fibers comprise fibers selected from glass fibers and stone wool fibers.

9. The composition of claim 8, wherein the mineral fibers comprise glass fibers.

10. The composition of claim 1, wherein the mixture of at least two reducing sugars is provided as high fructose corn syrup (HFCS).

11. The composition of claim 1, wherein the binder has a moisture content of 1.5-3%.

12. The composition of claim 1, wherein the binder has a pH of 7.5-9.5.

13. The composition of claim 1, wherein the mineral fibers comprise glass fibers at a compositional concentration of 80-99% by weight.

14. The composition of claim 1, wherein the binder compriscs has 5-25% by dry weight of an acid precursor derivable from an inorganic salt selected from the group consisting of ammonium sulfate salts, ammonium phosphate salts, ammonium nitrate salts, ammonium carbonate salts and combinations thereof.

15. The composition of claim 1, wherein the binder has 10-20% by dry weight of an acid precursor derivable from an inorganic salt selected from the group consisting of ammonium sulfate salts, ammonium phosphate salts, ammonium nitrate salts, ammonium carbonate salts and combinations thereof.

16. The composition of claim 1, wherein the aqueous mixture is a viscous or tacky liquid.

* * * * *